US00RE41920E

(19) United States
(12) Reissued Patent
Singh

(10) Patent Number: US RE41,920 E
(45) Date of Reissued Patent: Nov. 9, 2010

(54) ISOBUTYLGABA AND ITS DERIVATIVES FOR THE TREATMENT OF PAIN

(75) Inventor: Lakhbir Singh, Cambridgeshire (GB)

(73) Assignee: Warner-Lambert Company LLC, New York, NY (US)

(21) Appl. No.: 11/983,750

(22) PCT Filed: Jul. 16, 1997

(86) PCT No.: PCT/US97/12390

§ 371 (c)(1),
(2), (4) Date: Jul. 15, 1998

(87) PCT Pub. No.: WO98/03167

PCT Pub. Date: Jan. 29, 1998

Related U.S. Patent Documents

Reissue of:
(64) Patent No.: 6,001,876
Issued: Dec. 14, 1999
Appl. No.: 09/043,358
Filed: Jul. 15, 1998

(51) Int. Cl.
*A61K 31/195* (2006.01)

(52) U.S. Cl. ..... 514/561
(58) Field of Classification Search ..... None
See application file for complete search history.

(56) References Cited

U.S. PATENT DOCUMENTS

| | | | |
|---|---|---|---|
| 3,471,548 | A | 10/1969 | Keberle et al. |
| 4,024,175 | A | 5/1977 | Satzinger et al. |
| 4,087,544 | A | 5/1978 | Satzinger et al. |
| 4,123,438 | A | 10/1978 | Geurts et al. |
| 4,322,440 | A | 3/1982 | Fish et al. |
| 4,479,005 | A | 10/1984 | Kleschick |
| 5,023,269 | A | 6/1991 | Robertson et al. |
| 5,025,035 | A | 6/1991 | Wallace |
| 5,051,448 | A | 9/1991 | Shashoua et al. |
| 5,084,479 | A | 1/1992 | Woodruff |
| 5,104,869 | A | 4/1992 | Albright et al. |
| 5,492,927 | A | 2/1996 | Gitter et al. |
| 5,510,381 | A | 4/1996 | Pande |
| 5,563,175 | A | 10/1996 | Silverman et al. |
| 5,599,973 | A | 2/1997 | Silverman et al. |
| 5,608,090 | A | 3/1997 | Silverman et al. |
| 5,616,793 | A | 4/1997 | Huckabee et al. |
| 5,629,447 | A | 5/1997 | Huckabee et al. |
| 5,637,767 | A | 6/1997 | Grote et al. |
| 5,684,189 | A | 11/1997 | Silverman et al. |
| 5,710,304 | A | 1/1998 | Silverman et al. |
| 5,792,796 | A | 8/1998 | Woodruff et al. |
| 5,840,956 | A | 11/1998 | Grote et al. |
| 5,847,151 | A | 12/1998 | Silverman et al. |
| 5,929,088 | A | 7/1999 | Horwell et al. |
| 5,998,435 | A | 12/1999 | Horwell et al. |
| 6,020,370 | A | 2/2000 | Horwell et al. |
| 6,028,214 | A | 2/2000 | Silverman et al. |
| 6,046,353 | A | 4/2000 | Grote et al. |
| 6,054,482 | A | 4/2000 | Augart et al. |
| 6,103,932 | A | 8/2000 | Horwell et al. |
| 6,117,906 | A | 9/2000 | Silverman et al. |
| 6,127,418 | A | 10/2000 | Bueno et al. |
| 6,140,366 | A | 10/2000 | Silverman et al. |
| 6,194,459 | B1 | 2/2001 | Akunne et al. |
| 6,197,819 | B1 | 3/2001 | Silverman et al. |
| 6,242,488 | B1 | 6/2001 | Bueno et al. |
| 6,255,345 | B1 | 7/2001 | Silverman et al. |
| 6,262,120 | B1 | 7/2001 | Silverman et al. |
| 6,291,526 | B1 | 9/2001 | Silverman et al. |
| 6,306,910 | B1 | 10/2001 | Magnus |
| 6,326,374 | B1 | 12/2001 | Magnus et al. |
| 6,329,429 | B1 | 12/2001 | Schrier |
| 6,342,529 | B1 | 1/2002 | Silverman et al. |
| 6,359,005 | B1 | 3/2002 | Pande |
| 6,359,169 | B1 | 3/2002 | Silverman et al. |
| 6,372,792 | B1 | 4/2002 | Chouinard |
| 6,414,024 | B1 | 7/2002 | Silverman et al. |
| 6,426,368 | B2 | 7/2002 | Bueno et al. |
| 6,436,974 | B1 | 8/2002 | Belliotti et al. |
| 6,451,857 | B1 | 9/2002 | Hurtt et al. |
| 6,521,650 | B1 | 2/2003 | Belliotti et al. |
| 6,525,096 | B1 | 2/2003 | Silverman et al. |
| 6,544,998 | B2 | 4/2003 | Mylari |
| 6,566,400 | B1 | 5/2003 | Akunne et al. |
| 6,579,879 | B2 | 6/2003 | Mylari |
| 6,593,368 | B2 | 7/2003 | Magnus-Miller et al. |
| 6,596,900 | B2 | 7/2003 | Blakemore et al. |
| 6,605,745 | B2 | 8/2003 | Hoge et al. |
| 6,642,398 | B2 | 11/2003 | Belliotti et al. |
| 6,680,343 | B1 | 1/2004 | Angello |
| 6,689,915 | B2 | 2/2004 | Hoge et al. |
| 6,703,522 | B2 | 3/2004 | Blakemore et al. |
| 6,713,490 | B2 | 3/2004 | Kawamura |
| 6,720,348 | B2 | 4/2004 | Mylari |
| 6,730,674 | B2 | 5/2004 | Martin et al. |

(Continued)

FOREIGN PATENT DOCUMENTS

| | | |
|---|---|---|
| CA | 1304080 | 6/1992 |
| CA | 2265615 | 3/1998 |
| CA | 2530904 | 6/2007 |

(Continued)

OTHER PUBLICATIONS

Lever et al (in Annual Reports in Medicinal Chemistry, vol. 19: p. 5, 1984).*

Berge et al (J Pharm Sci 66:1–19, 1977).*

Plea (response) of ANVISA and INPI relating to Brazillan patent application P19710536–8 dated Oct. 5, 2009 (date on last page) (in Portugese).

(Continued)

*Primary Examiner*—Sreeni Padmanabhan
*Assistant Examiner*—Craig Ricci
(74) *Attorney, Agent, or Firm*—Connolly Bove Lodge & Hutz LLP

(57) ABSTRACT

The instant invention is a method of using certain analogs of glutamic acid and gamma-aminobutyric acid in pain therapy.

23 Claims, 18 Drawing Sheets

U.S. PATENT DOCUMENTS

| | | | |
|---|---|---|---|
| 6,750,171 | B2 | 6/2004 | Hoge et al. |
| 6,849,629 | B2 | 2/2005 | Mylari |
| 6,855,849 | B2 | 2/2005 | Hoge et al. |
| 6,887,902 | B2 | 5/2005 | Schrier |
| 6,891,059 | B2 | 5/2005 | Burk et al. |
| 6,894,047 | B2 | 5/2005 | Mylari |
| 6,924,377 | B2 | 8/2005 | Blazecka et al. |
| 6,942,876 | B2 | 9/2005 | Magnus-Miller et al. |
| 6,992,109 | B1 | 1/2006 | Segal et al. |
| 7,022,678 | B2 | 4/2006 | Hurley et al. |
| 7,026,505 | B2 | 4/2006 | Dooley et al. |
| 7,030,119 | B1 | 4/2006 | Barrett et al. |
| 7,053,122 | B2 | 5/2006 | Maw et al. |
| 7,067,262 | B2 | 6/2006 | Su |
| 7,071,339 | B2 | 7/2006 | Belmont et al. |
| 7,074,814 | B2 | 7/2006 | Para et al. |
| 7,122,683 | B2 | 10/2006 | Fish et al. |
| 7,138,406 | B2 | 11/2006 | Chantigny et al. |
| 7,138,542 | B2 | 11/2006 | Dooley et al. |
| 7,141,695 | B2 | 11/2006 | Przewosny et al. |
| 7,164,034 | B2 | 1/2007 | Dooley et al. |
| 7,205,295 | B2 | 4/2007 | Barvian et al. |
| 7,214,824 | B2 | 5/2007 | Inoue et al. |
| 7,217,721 | B2 | 5/2007 | Basford et al. |
| 7,230,135 | B2 | 6/2007 | Hoge, II et al. |
| 7,235,363 | B2 | 6/2007 | Bertelli et al. |
| 7,235,657 | B2 | 6/2007 | Li |
| 7,256,216 | B2 | 8/2007 | Kulkarni et al. |
| 7,279,486 | B2 | 10/2007 | Hashizume et al. |
| 7,309,719 | B1 | 12/2007 | Aomatsu |
| 7,354,925 | B2 | 4/2008 | Hashizume et al. |
| 7,381,747 | B2 | 6/2008 | Dooley et al. |
| 7,390,931 | B2 | 6/2008 | Hoge, II |
| 7,414,156 | B2 | 6/2008 | Hoge, II et al. |
| 7,419,981 | B2 | 9/2008 | Field et al. |
| 7,423,054 | B2 | 9/2008 | Yuen |
| 7,425,569 | B2 | 9/2008 | Bradley et al. |
| 7,482,375 | B2 | 1/2009 | Bradley et al. |
| 7,485,636 | B2 | 2/2009 | Yuen |
| 7,491,835 | B2 | 2/2009 | Donevan et al. |
| 7,507,742 | B2 | 3/2009 | Rawson et al. |
| 7,514,457 | B2 | 4/2009 | Inoue et al. |
| 7,547,714 | B2 | 6/2009 | Cheng et al. |
| 7,553,877 | B2 | 6/2009 | Chantigny et al. |
| 7,566,739 | B2 | 7/2009 | Hanazawa et al. |
| 7,569,572 | B2 | 8/2009 | Bell et al. |
| 7,572,797 | B2 | 8/2009 | Denton et al. |
| 7,572,799 | B2 | 8/2009 | Bell et al. |
| 7,572,910 | B2 | 8/2009 | Mylari |
| 7,579,471 | B2 | 8/2009 | Basford et al. |
| 7,589,109 | B2 | 9/2009 | Uchida et al. |
| 7,595,329 | B2 | 9/2009 | Ando et al. |
| 7,598,231 | B2 | 10/2009 | Cheng et al. |
| 7,598,393 | B2 | 10/2009 | Kon-I et al. |
| 7,612,226 | B2 | 11/2009 | Graham et al. |
| 7,622,589 | B2 | 11/2009 | Hanazawa et al. |
| 7,649,004 | B2 | 1/2010 | Lane et al. |
| 7,659,305 | B2 | 2/2010 | Rawson |
| 7,659,394 | B2 | 2/2010 | Barta et al. |
| 2001/0036943 | A1 | 11/2001 | Coe et al. |
| 2002/0058706 | A1 | 5/2002 | Schrier et al. |
| 2002/0072533 | A1 | 6/2002 | Schrier et al. |
| 2003/0045449 | A1 | 3/2003 | Lowe et al. |
| 2003/0045500 | A1 | 3/2003 | Magnus et al. |
| 2004/0002543 | A1 | 1/2004 | Magnus et al. |
| 2004/0006073 | A1 | 1/2004 | Dooley |
| 2004/0092522 | A1 | 5/2004 | Field et al. |
| 2004/0097405 | A1 | 5/2004 | Schrier et al. |
| 2004/0132636 | A1 | 7/2004 | Dooley et al. |
| 2004/0138305 | A1 | 7/2004 | Taylor, Jr. et al. |
| 2004/0143014 | A1 | 7/2004 | Bertrand et al. |
| 2005/0004106 | A1 | 1/2005 | Romano |
| 2005/0004177 | A1 | 1/2005 | Roark |
| 2005/0059654 | A1 | 3/2005 | Arneric et al. |
| 2005/0059715 | A1 | 3/2005 | Dooley et al. |
| 2005/0065176 | A1 | 3/2005 | Field et al. |
| 2005/0148573 | A1 | 7/2005 | Katsu et al. |
| 2005/0171203 | A1 | 8/2005 | Meyer-Wonnay et al. |
| 2005/0182049 | A1 | 8/2005 | Howard |
| 2005/0222464 | A1 | 10/2005 | Hoge |
| 2005/0228190 | A1 | 10/2005 | Bao et al. |
| 2005/0277672 | A1 | 12/2005 | Ando et al. |
| 2005/0283023 | A1 | 12/2005 | Hu et al. |
| 2006/0003344 | A1 | 1/2006 | Houseknecht et al. |
| 2007/0191350 | A1 | 8/2007 | Field et al. |
| 2007/0191462 | A1 | 8/2007 | Hettiarachchi et al. |
| 2007/0196905 | A1 | 8/2007 | Burns et al. |
| 2008/0293746 | A1 | 11/2008 | Gunn |
| 2009/0036487 | A1 | 2/2009 | Field et al. |
| 2009/0156677 | A1 | 6/2009 | Aomatsu |
| 2009/0170897 | A1 | 7/2009 | Corradini et al. |
| 2009/0318451 | A1 | 12/2009 | Ackley |
| 2010/0035880 | A1 | 2/2010 | Hanazawa et al. |

FOREIGN PATENT DOCUMENTS

| | | |
|---|---|---|
| EP | 024965 | 4/1983 |
| EP | 088593 | 9/1983 |
| EP | 181833 | 5/1986 |
| EP | 0 300 448 | 1/1989 |
| EP | 0 353 350 | 2/1990 |
| EP | 0368766 | 5/1990 |
| EP | 399949 | 11/1990 |
| EP | 0414263 | 2/1991 |
| EP | 419247 | 3/1991 |
| EP | 0446 570 | 9/1991 |
| GB | 2126224 | 3/1984 |
| JP | 49-40460 | 11/1974 |
| JP | 07 215863 A | 8/1995 |
| WO | WO 85/00520 | 2/1985 |
| WO | WO92/09560 | 6/1992 |
| WO | WO92/009560 | 6/1992 |
| WO | WO 92/14443 | 9/1992 |
| WO | WO 93/12811 | 7/1993 |
| WO | WO93/23383 | 11/1993 |
| WO | WO93/023383 | 11/1993 |
| WO | WO 94/25016 | 11/1994 |
| WO | WO 95/32730 | 12/1995 |
| WO | WO 96/003122 | 2/1996 |
| WO | WO96/011680 | 4/1996 |
| WO | WO96/015782 | 5/1996 |
| WO | WO96/021661 | 7/1996 |
| WO | WO96/026929 | 9/1996 |
| WO | WO 97/29101 | 8/1997 |
| WO | WO 97/39768 | 10/1997 |
| WO | WO 98/58641 | 12/1998 |
| WO | WO99/059572 | 11/1999 |
| WO | WO99/059573 | 11/1999 |
| WO | WO00/061234 | 10/2000 |
| WO | WO01/001983 | 1/2001 |
| WO | WO01/024791 | 4/2001 |
| WO | WO01/024792 | 4/2001 |
| WO | WO2005/102389 | 11/2005 |
| WO | WO2005/102390 | 11/2005 |
| WO | WO06/008640 | 1/2006 |
| WO | WO06/092692 | 9/2006 |
| WO | WO06/123247 | 11/2006 |
| WO | WO07/052125 | 5/2007 |
| WO | WO07/102058 | 9/2007 |

OTHER PUBLICATIONS

English Translation of document C1.

Notificacao n. * 204/09 for PI 9710536–8 (Notification Regarding the Decision to Deny Prior Approval by ANVISA on May 13, 2009) (in Portuguese).

English Translation of document C3.

Andruszkiewcz et al., Chemoenzymatic Synthesis of (R)–And (S)–4–Amino–3–Methylbutanoic Acids; Synthetic Comm. (1990) 20(1): 159–166.

Audus et al., *Characteristics of the Large Neutral Amino Acid Transport System of Bovine Brain Microvessel Endothelial Cell Monolayers*, Journal Of Neurochemistry (1986) 47(2):484–488.

Bartoszyk et al, *Gabapentin*, Current Problems In Epilepsy, New Anticonvlsant Drugs (1986) 4:147–163.

Burger, Alfred, *A Guide to the Chemical Basis of Drug Design*, John Wiley & Sons, Inc., A Wiley–Interscience publication; Chapter 2 *Recent Active Research Areas*; (1983) 37–91.

Buu et al., *Biological Actions in vivo of two y–aminobutyric acid (GABA) Analogues : B–chloro Gaba and B–Phenyl Gaba* ; Br. J. Pharmacol. (1974) 52 : 401–406.

Colonge et al, *Preparation of 2–Pyrrolidones and y–Amino Acids*, Bulletin De La Societe Chimique De France (1962) 598–603.

Crawford et al., Gabapentin as an antiepileptic drug in man, *J. Neurology Neurosurgery and Psychiatry*, (1987) 50:682–686.

Korsgaard, "Bacolfen (Lioresal) in the treatment of neuroleptic–induced tardive dyskinesia", (1976) 54:17–24.

Karlsson, et al; *Effect of the Convulsive agent 3–mercaptopropionic acid on the levels of GABA, other amino acids and glutamate decarboxylase in different regions of the rat brain*; Biochem. Pharmacol (1974) 23:3053–3061.

Krall, R.L., et al., *Antiepileptic drug development: II.Anticonvulsant drug screening*, Epilepsia (1978) 19:409–428.

Litchfield, J.T. and Wilcoxon, F.; *A simplified method of evaluating dose–effect experiments*, Journal Of Pharmacology And Experimental Therapeutics (1949) 96: 99–113.

Loscher and Schmidt, *Which animal models should be used in the search for new antiepileptic drugs? A proposal based on experimental and clinical considerations*, Epilepsy Research (1988) 2(3): 145–181.

Komissarov, S.I., "*Non–opiate Subarachnoidal Analgesia Induced by GABA–Positive Substances*", Farmakologiia, Toksikologiia Problemy Toksikologii (1985) 48(4): 54–58.

Jurna et al., *Antikonvulsiva beim Nervenschmerz(Anticonvulsant agents in neuralgic pain)*, Abstract, Institut fur Pharmakologie und Toxikologie der Universitat des Saarlandes, W–6650, Homburg/Saar, Bundesrepublik Deutschland ; Der Schmerz (1992) 6: 146–149.

Kopelvich, "*Advances in the Search for Medicinal Drugs Based on y–Aminobutyric Acid*", Russian Chemical Reviews (1979) 48(7): 679–691.

Zobacheva et al.; The Interaction of Nitroolefins With Malonic Dimethyl Ester; Higher Education Scientific Reports; Chemistry and Chemical Technology; No. 4; pp. 740–742 (1958).

Nicoll, "The Effect of Conformationally Restricted Amino Acid Analogues on the Frog Spinal Cord in vitro", *Br. J. Pharm.*, (1977) 59: 303–309.

Pardridge, *Strategies for Drug Delivery through the Blood Brain Barrier*, Directed Drug Delivery, Borchardt, Repta and Stella, eds. Humana Press, Clifton, New Jersey, (1985) pp. 83–96.

Perekalin & Zobacheva, "*Synthesis Of y–Amino Acids And Pyrrolidones*," J. Gen. Chem. USSR (1959) 29: 2865–2869.

Pierdda et al., *Effect of stimulus intensity on the profile of anticonvulsant activity of phenytoin, ethosuximide and valproate*, Journal Of Pharmacology And Experimental Therapeutics (1985) 232(3): 741–745.

Purpura et al., Structure–Activity Determinants of Pharmacological Effects of Amino Acids and Related Compounds on Central Synapses, J. Neurochem. (1959) 3:238–268.

Saletu et al., "*Evaluation of encephalotropic and psychotropic properties of gabapentin in man by pharmaco–EEG and psychometry*", Int. J. Clin. Pharmacol Ther Toxcol, (Jul. 1986) 24(7):362–373.

Silverman et al., *Substituted 4–Aminobutanoic Acids: Substrates For y–Aminobutyric Acid α–Ketoglutaric Acid Aminotransferase, J. Bio. Chem.*(Nov. 1981) 256(22): 11565–11568.

Silverman et al., *Substrate Stereospecificity and Active Site Topography of y–Aminobutyric Acid Aminotransferase for β–Aryl–y–aminobutyric Acid Analogues, J. Bio. Chem.*, (1987) 262(7): 3192–3195.

Smith et al., *Kinetics of Neutral Amino Acid Transport Across the Blood–Brain Barrier*, Journal Of Neurochemistry, (1987) 49(5): 1651–1658.

Swinyard et al., "*General Principles: Experimental Selection, Qualification, and Evaluation of Anticonvulsants," Antiepileptic Drugs, Third Edition*, edited by R. Levy et al., Raven Press, Ltd., New York, (1989) 85–102.

Taylor, et al., "3–Alkyl GABA and 3–Alkylglutamic Acid Analogues: Two New Classes of Anticonvulsant Agents", Epilepsy Res., (1992) 11: 103–110.

Zapp, "Postpoliomyelitis Pain Treated with Gabapentin", American Family Physician, (1996) 53(8), pp. 2442 and 2445.

Baxter, C.F and Roberts, E.; *The y–Aminobutyric Acid–a–Ketoglutaric Acid Transaminase of Beef Brain*; J. Biol. Chem. (1958) 233(5): 1135–1139.

Butterworth J, et al, *Phosphate–Activated Glutaminase in Relation to Huntington's Disease and Agonal State* ; J. Neurochem. (1983);41(2):440–447.

Campbell, et al., *Clinical trial of carbamazepine in trigeminal neuralgia*, J. Neuro. Neurosurg. Psychiat. (1966) 29: 265–267.

Carvajal G, et al, *Anticonvulsive Action of Substances Designed as Inhibitors of y–Aminobutyric Acid–a–Ketoglutaric Acid Transaminase* ; Biochem. Pharmacol. (1964) 13:1059–1069.

Chadwick, *Recent Advances in Epilepsy*, Pedley T A, Meldrum B S, (eds.) Churchill Livingstone, New York (1991) 5: 211–222.

Gee, et al., *The Novel Anticonvulsant Drug, Gabapentin (Neurontin)*, Binds to the $\alpha_2$ σSubunit of a Calcium Channel , J Biol. Chem., (Mar. 1996) 271(10), 5768–5776.

Sobocinska et al.; Resolution of Racemic β–Phenyl–y–Aminobutyric Acid Into Its Enantiomers and Determination of Their Absolute Configuration; Roczniki Chemii 48; pp. 461–465 (1974).

Hayashi; *The inhibitory action of β–Hydroxy–y–Aminobutyric Acid Upon the Seizure following Stimulation of the Motor Cortex of the Dog*; J. Physiol. (London) (1959) 145:570–578.

A.F. Casy; Stereochemistry and Biological Activity; (7) from Medicinal Chemistry (3rd Edition) Part 1; Editor Alfred Burger; Wiley–Interscience; Cover pages and pp. 81–107 (1970).
Iversen, et al, Psychiatry Research (1974)11:255–256.
Janssens de Varebeke, et al, *Effect of Milacemide, A Glycinamide Derivative, on the rat Brain y–Aminobutyric Acid System* ; Biochem. Pharmacol. (1983)32(18):2751–2755.
Kaplan, "New Anticonvulsants: Schiff Bases of y–Aminobutyric Acid and y–Aminobutyramide", J. Med. Chem., (1980)23: 702–704.
Loscher, Anticonvulsant and Biochemical Effects of Inhibitors of GABA Aminotranserase and Valproic Acid During Subchronic Treatment in Mice; Biochem. Pharmacol. (1982) 31(5):837–842.
Mackin, *Medical and pharmacologic management of upper extremity neuropathic pain syndromes*; J Hand Therapy (Apr./Jun. 1997)10(2) 96–109.
Mao et al., *Gabapentin in Pain Management*; Anesth Analg (2000)91 :680–7.
McGeer, et al., GABA and Glutamate Enzymes; Glutamine, Glutamate, and GABA in the Central Nervous System; Eds Liss: New York (1983) 3–17.
McGeer et al., *The GABA System and Function of the Basal Ganglia: Huntington's Disease*; GABA in Nervous System Function; Roberts et al., Eds., Raven Press: New York (1976) 487–495.
Meldrum, et al, Neuronal Inhibition Mediated by GABA and Patterns of Convulsions in Baboons with Photosensitive Epilepsy (Papio Papio); Epilepsy; Harris et al., Eds., Churchill Livingston (1974) 55–64.
Mellick et al., *The use of gabapentin in the treatment of reflex sympathetic dystrophy and a phobic disorder*. Am J Pain Manage (1995) 5(1):7–9.
Phillips et al., The effects of sodium valproate on y–aminobutyrate metabolism and behaviour in naive and ethanolamine–o–sulphate pretreated rats and mice ; Biochem. Pharmacol. (1982) 31(13):2257–2261.
Roberts et al., GABA in Nervous System Function, Raven Press: New York, 1976 (Table of Contents only).
Rock et al., *Gabapentin actions on ligand– and voltage–gated responses in cultured rodent neurons*. Epilepsy Res. (1993) 16: 89–98.
Shashoua et al., y–Aminobutyric Acid Esters. 1. Synthesis, Brain Uptake, and Pharmacological Studies of Aliphatic and Steroid Esters of y–Aminobutyric Acid; J. Med. Chem. (1984)27:659–664.
Silverman R. B., *Mechanism–Based Enzyme Inactivation: Chemistry and Enzymology*, vol. I and II, CRC: Boca Raton (1988).
Sist et al., *Gabapentin for idiopathic trigeminal neuralgia: report of two cases*. Neurology, (1997)48: 1467–1471.
Spokes, GABA in Huntington's Chorea, Parkinsonism and Schizophrenia; Adv. Exp. Med. Biol. (1978)123:461–473.
Steinman et al.; Narrative Review:The Promotion of Gabapentin: An Analysis of Internal Industry Documents; Annals of Internal Medicine, 145(4), pp. 284–293 (2006).
Tomson, et al., *Carbamazepine in Trigeminal Neuralgia: Clinical Effects in Relation to Plasma–Concentration*, Upsala J. Med. Sci., Suppl., (1980) 31: 45–46.
Xiao and Bennett, in *Gabapentin Relieves Abnormal Pains in A Rat Model Of Painful Peripheral Neuropathy*, Society For Neuroscience Abstracts (1995) 21(2):356.17.
Waldman S D, Tutorial 28: Evaluation and Treatment of Trigeminal Neuralgia. Pain Digest (1997) 7(1):21–24.
Wetzel et al., *Use of gabapentin in pain management*. The Annals of Pharmacotherapy; (Sep. 1997)31: 1082–3.
Wu et al., Abnormalities of Neurotransmitter Enzymes in Huntington's Chorea; Neurochem. Res. (1979)4(5):575–586.
Yurovskaya and Borschheva, in *Psychoemotional Regulation and Labor Pain Relief During Phenibut Administration*, Voprosy Okhrany Materinstava I Detstva (1990) 35(5):55–58.
Yoon Kim et al.; Glutamic Acid Analogs. The Synthesis of 3–Alkylglutamic Acids and 4–Alkylpyroglutamic Acids; J. Med. Chem., 8(4), 509–513 (1965).
Cronin et al.; Gas Chromatographic–Mass Spectral Analysis of the Five–Carbon β–, y–, and σ–Amino Alklanoic Acids, Analytical Biochemistry 124, pp. 139–149 (1982).
Silverman, "4–Amino–2(substituted methyl)–2–butenoic Acids: Substrates and Potent Inhibitors of GABA Aminotransferase", J. Med. Chem., (1986)29: 764–770.
Silverman, "From Basic Science to Blockbuster Drug: The Discovery of Lyrica", *Angew. Chem. Int. Ed.*, (2008) 47:3500–3504.
Andruszkiewicz, et al., "A Convenient Synthesis of 3–Alkyl–4–aminobutanoic Acids", Synthesis, Journal of Synthetic Organic Chemistry (Dec. 1989) 953–955.
Field, et al., "*Gabapentin(Neurontin) and S–(+)–3–Isobutylgaba Represent a Novel Class of Selective Antihyperalgesic Agents*", British J. Pharmacol., (1997) 121: 1513–1522.
McQuay, et al., "*Anticonvulsant Drugs for the Management of Pain: A Systematic Review*", BMJ, (Oct. 1995) 311: 1047–1052.
Mellick, et al., "Gabapentin in the Management of Reflex Sympathetic Dystrophy"; J. Pain Symptom Management, (1995) 10 (4): 265–266.
Mellick, "Successful Treatment of Reflex Sympathetic Dystrophy with Gabapentin"; Am. J. Emerg. Med., (1995) 96.
Mellick, et al., "Reflex Sympathetic Dystrophy Treated with Gabapentin", Arch. Phys. Med. Rehabil., (1997) 78: 98–105.
Rosner, et al., "Gabapentin Adjunctive Therapy in Neuropathic Pain States", Clin. J. Pain, (1996) 12 (1): 56–58.
Segal, et al., "Gabapentin as a Novel Treatment for Postherpetic Neuralgia", American Academy of Neurology, (1996) 46(4): 1175–1176.
Suman–Chauhan, et al., "Characterisation of [$^3$H]gabapentin Binding to a Novel Site in Rat Brain; Homogenate Binding Studies", Eur. Jr. Pharmacol., (1993) 244 (3): 293–301.
Taylor, et al., "*Potent and Stereospecific Anticonvulsant Activity of 3–Isobutyl GABA Relates to in Vitro Binding at a Novel Site Labeled by Tritiated Gabapentin*", Epilepsy Res., (1993)14: 11–15.
Thurlow, et al., "[3H]Gabapentin May Label a System–L–Like Neurtral Amino Acid Carrier in Brain", European Journal of Pharmacology, (1993)247:341–345.
Certified English Language Translation of document B1.
Certified English Language Translation of document C6.
Certified English Language Translation of document C13.
Certified English Language Translation of document C14.
Certified English Language Translation of document C16.
Certified English Language Translation od document C63.
U.S. Appl. No. 60/559,194.
U.S. Appl. No. 10/018,616, Brummel et al.
U.S. Appl. No. 60/142,215.
U.S. Appl. No. 10/089,958, Hughes et al.

U.S. Appl. No. 60/158,271.

U.S. Appl. No. 10/089,819, Hughes et al.

U.S. Appl. No. 08/445,398, Woodruff et al.

U.S. Appl. No. 08/25,5143.

U.S. Appl. No. 08/924,779.

Goodman and Gilman's The Pharmacological Basis of Therapeutics, 8$^{th}$ Edition, Chapter 19, Figure 19–1 (1990).

Presentation at the Indiana Chapter RSDS [Reflex Sympathetic Dystrophy Syndrome] Symposium on Aug. 13, 1994.

Poster presentation entitled "Successful Treatment of Reflex Sympathetic Dystrophy with Gabapentin (Neurontin)", at the 13$^{th}$ Annual Scientific Meeting of the American Pain Society in Miami Beach, Florida, on Nov. 10–13, 1994.

Sist et al., Gabapentin for Idiopathic Trigeminal Neuralgia; Report of Two Cases, Neurology, May 1997 48:1467.

Burger A., Medicinal Chemistry, John Wiley & Sons, 1970, pp. 81, 83.

Handley, S.L. and Singh, L. (1985). Modulation of 5–hydroxytryptamine–induced head–twitch response by drugs acting at GABA and related receptors. *Br. J. Pharmacol.*, 86, 297–303.

Singh, L. Heaton, C.J.P., Rea, P.J. and Handley, S.L. (1986), Involvement of noradrenaline in potentiation of the head–twitch response by GABA–related drugs. *Psychopharmacol.*88, 315–319.

Handley, S.L., and Singh, L. (1986) The modulation of head–twitch behaviour by drugs acting on the beta–adrenoceptors. Evidence for involvement of both $beta_1$–and $beta_2$_adrenoceptors. *Psychopharmacol.*88, 320–324.

Handley, S.L. and Singh, L. (1986). Involvement of Locus Coeruleus in the potention of the quipazine head–twitch response by diazepam and beta–adrenceptor agonists. *Neuropharmacol.*, 25, 1315–1321.

Handley, S.L. and Singh, L. (1986). Chronic antidepressant treatment reduces central β–adrenoceptor sensitivity in a behaviour test. *Eur. J. Pharmacol.* 127, 97–103.

Singh, L. and Handley, S.L. (1987). Behavioural evidence for an interdependence between GABAa receptors and $Beta_2$_adrenoceptors. *Eur. J. Pharmacol.*, 135, 419–421.

Handley, S.L., and Singh, L. (1986) Neurotransmitters and shaking behaviour–more than a 'gut–bath' for the brain? *Trends Pharmacol. Sci.*, 7, 324–328.

Tricklebank, M.D., Singh, L., Oles, R.J., Wong, E.H.F. and Iversen, S.D. (1987). A role for receptors of N–methyl–D–aspartic acid in the discriminative stimulus properties of phencyclidine. *Eur. J. Pharmacol.*, 141, 497–501.

Price, B.W., Ahier, R.G., Middlemiss, D.N., Singh, L., Tricklebank, M.D., and Wong, E.H.F. (1988). In vivo labeling of the NMDA receptor channel complex by [$^3$H] MK–801. *Eur. J. Pharmacol.*, 158, 279–282.

Iversen, S.D., Singh, L., Oles, R.J., Preston, C. and Tricklebank, M.D. (1988). Psychophamacological profile of the N–methyl–D–aspartate (NMDA) receptor antagonist, MK–801. In Sigma and Phencyclidine–Like Compounds as Molecular Probes in Biology, edited by E.F. Domino and J.M. Kamenka pp. 373–382.

Tricklebank, M.D., Singh, L., Oles, R.J., Preston, C. and Iversen, S.D. (1989). The behavioural effects of MK–801: a comparison with antagonists acting non–competitively and competively at the NMDA receptor. *Eur. J. Pharmacol.*, 167, 127–135.

Singh, L., E.H.F., Kesingland, A. and Tricklebank, M.D. (1990). Evidence against an involvement of the haloperidol–sensitive sigma recognition site in the discriminative stimulus properties of (+)–N–allyl–normeta30cine (+)–SKF–10, 047). *Br. J. Pharmacol.*99, 145–151.

Singh, L., Oles, R.J. and Tricklebank, M.D. (1990). Modulation of seizure susceptibility in the mouse by the strychnine–insensitive glycine recognition site of the NMDA receptor/ion channel complex. *Br. J. Pharmacol.*, 99, 285–288.

Singh, L. Donald, A.E., Foster, A.C., Hutson, P.H., Iversen, L.L., Iversen, S.D., Kemp, J.A., Leeson, P.D., Marshall, G.R., Oles, R.J., Priestley, T., Thorn, L., Tricklebank, M.D., Vass, C.A. and Williams, B.J. (1990), Enantiomers of HA–966 (3–amino–1–hydroxpyrrolid–2–one) exhibit distinct central nervous system effects: (+) —HA–966 is a selective glycine/N–methyl–D–aspartate receptor antagonist, but (–)–HA 966 is a potent gamma–butyrolactone–like sedative, *Proc. Natl. Acad. Sci.*, U.S.A. 87, 347–351.

Singh, L., Menzies, R. and Tricklebank, M.D. (1990). The discriminative stimulus properties of (+)–HA–966, an antagonist at the glycine/N–methyl–D–aspartate receptor. *Eur. J. Pharmacol.*, 186, 129–132.

Tricklebank, M.D., Honore, T., Iversen, S.D., Kemp, J.A., Knight, A.R., Marshall, G.R., Rupniak, N.M.J., Singh, L., Tye, S., Watjen, F. and Wong, E.H.F. (1990). The pharmacological properties of the imidazobenzodiazepine, FG 8205, a novel partial agonist at the benzodiazepine receptor. *Br. J. Pharmacol.*, 101, 753–761.

Thompson, W. J., Anderson, P.S., Britcher, S.F., Lyle, T.A., Thies, J.E. Magill, C.A., Varga, S.L., Schwering, J.E, Lyle, P.A., Christy, M.E., Evans, B.E., Colton, C.D., Holloway, M.K., Springer, J.P., Hirshfield, J.M., Ball, R.G., Amato, J.S., Larsen, R.D., Wong, E.H.F., Kemp, J.A., tricklebank, M.D., Singh, L., Oles, R.J., Priestly, T., Marshall, G.R, Knight, A.R., Middlemiss, D.N., Woodruff, G.N., and Iversen, L.L. (1990). Synthesis and pharmacological evaluation of a series of dibenzo([a,s])cycloalkenimines as N–methyl–D–aspartate antagonists. *J. Med. Chem.*, 33, 789–808.

Singh, L. Oles, R. and Woodruff, G. (1990). In vivo interaction of a polyamine with the NMDA receptor. *Eur. J. Pharmacol.*, 180, 391–392.

Singh, L., C.A., Hunter, J.C., Woodruff, G.N. and Hughes, J. (1990). The anticonvulsant action of CI–977, a selective kappa–opioid receptor agonist: a possible involvement of the glycine/NMDA receptor complex. *Eur. J. Pharmacol.*, 191, 477–480.

Singh, L., Lewis A.S., Field, M.J., Hughes, J. and Woodruff, G.N. (1991). Evidence for an involvement of the brain cholecystokinin B receptor in anxiety. *Proc. Natl. Acad. Sci.*, U.S.A. 88, 1130–1133.

Singh, L., Oles, R.J., Vass, C.A. and Woodruff, G.N. (1991). A slow intravenous infusion of N–methyl–DL–aspartate as a seizure model in the mouse. *J. Neurosci. Meth.*, 37, 227–232.

Hill, D.R., Singh, L., Boden, P., Pinnock, R., Woodruff, G.N. and Hughes, J. (1992). Detection of CCK receptor subtypes in mammalian brain using selective non–peptide antagonists. In Multiple Cholecystokinin Receptors in the CNS. Edited by Dourish, C. T., Cooper, S.J., Iversen, S.D. and Iversen L.L. Oxford University Press, pp. 57–76.

Woodruff, G.N., Hill, D., Boden,P., Pinnock, R., Singh, L. and Hughes, J. (1991). Functional role of brain CCK receptors. *Neuropeptides*, 19, (Suppl.), 45–56.

Singh., L., Field, M.J., Hughes, J., Oles, R.J., Vass, C.A. and Woodruff, G.N. (1991). The behavioural properties of CI–988, a selective CCK–B receptor antagonist. *Br. J. Pharmacol.*, 104, 239–245.

Tricklebank, M.D., Singh, L., Jackson, A. and Oles, R.J. (1991). Evidence that a proconvulsant action of lithium is mediated by inhibition of myo–inositol phosphatase in mouse brain. *Brain Res.*, 558, 145–148.

Singh, L., Field, M.J., Vass, C.A., Hughes, J. and Woodruff, G.N. (1992). The antagonism of benzodiazepine withdrawal effects by the selective cholecystokinin–B receptor antagonist CI–988. *Br. J. Pharmacol.*, 105, 8–10.

Boden, P.R., Higgenbottom, M., Hill, D.R., Horwell, D.C., Hughes, J., Rees, D.C., Roberts, E., Singh, L., Suman–Chauhan, N., and Woodruff, G.N. (1993). Cholecystokinin dipeptoid antagonists: Design, synthesis and anxiolytic profile of some novel CCK–A and CCK–B selective and "mixed" CCK–A/CCK–B antagonists. *J. Med. Chem.*, 36, 552–565.

Moore, K.W., Leeson, P.D., Carling, R.W., Tricklebank, M.D. and Singh, L. (1993). Anticonvulsant activity of glycine–site NMDA antagonists. 1.2–Carboxyl prodrugs of 5,7–dichlorokynurenic acid. *Bioorganic& Med. Chem. Lett.*, 3, 61–64.

Hunter, J.C. and Singh, L. (1994). Role of excitatory amino acid receptors in the mediation of the nociceptive response to formalin in the rat. *Neurosci. Lett.*174, 217–221.

Hunter, J.C., Atwal, P., Woodruff, G.N. and Singh, L. (1994). Differential modulation of κ and μ opoioid antinociception by the glycine/NMDA receptor agonist D–serine. *Br. J. Pharmacol.*, 112, 1002–1003.

Tricklebank, M.D., Bristow, L.J., Hutson, P.H., Leeson, P.D., Rowley, M.Saywell, K., Singh, L., Tattersall, F.D., Thorn, L. and Williams, B.J. (1994). The anticonvulsant and behavioural profile of L–687,414, a partial agonist acting at the glycine modulatory site on the N–methyl–D–aspartate (NMDA) receptor complex. *Br. J. Pharmacol.*, 113, 729–736.

Singh, L., Field, M.J., Hill, D.R, Horwell, D.C., McKnight, A.T., Roberts, E., Tang, K.W. and Woodruff, G.N. (1995). Peptoid CCK receptor antagonists: pharmacological evaluation of $CCK_{A1}$ $CCK_B$ and mixed $CCK_{A/B}$ receptor antagonists. *Eur. J. Pharmacol.*, 286, 185–191.

Singh, L., Oles, R.J., Field, M.J., Atwal, P. Woodruff, G.N. and Hunter, J.C., (1996). Effect of CCK receptor antagonists on the antinociceptive, reinforcing and gut motility properties of morphine. *Br. J. Pharmacol.*, 118, 1317–1325.

Singh, L., Field, M.J., Hunter, J.C., Oles, R.J. and Woodruff, G.N. (1996). Modulation of the in vivo actions of morphine by the mixed $CCK_{A/B}$ receptor antagonist PD 142898. *Eur. J. Pharmacol.*307, 283–289.

Singh, L., Field, M.F., Ferris, P., Hunter, J.C., Oles, R.J., Williams, R.G. and Woodruff, G.N. (1996). The Antiepileptic Agent Gabapentin (Neurontin) Possesses Anxiolytic–Like and Antinociceptive Actions that are Reversed by D–serine. *Psychopharmacol.*, 127, 1–9.

Brown, J.P., Boden, O., Singh, L. and Gee, N.S. (1996). Mechanisms of action of gabapentin (Neurontin). *Rev. Contem. Pharmacother.*, vol. 7, No. 5, 203–214.

Singh, L., Field, M.J., Hughes, J., Kuo, B.–S., Suman–Chauhan, N., Tuladhar, B.R., Wright, D.S. and Naylor, R.J. The tachykinin $NK_1$ receptor antagonist PF 154075 blocks cisplatin–induced delayed emesis in the ferret. *Eur. J. Pharmacol.*, 321, 209–216 (1997).

Field, M.J., Oles, R.J., Lewis, A.S., McCleary, S., Hughes, J. and Singh, L. (1997). Gabapentin (Neurontin) and S–(+)–3–isobutylgaba represent a novel class of selective antihyperalgesic agents. *Br. J. Pharmacol.*, (1997) 121, 1513–1522.

Stanfa, L.C., Singh, L., Williams, R.G. and A.H. Dickenson (1997). Gabapentin (Neurontin), ineffective in normal rats, markedly reduces C–fibre evoked responses after inflammation. *Neuroreport*, 8, 587–590 (1997).

Field, M.J., Holloman, E.F., McCleary, S., Hughes, J., Singh, L. Evaluation of gabapentin and S–(+)–3–isobutylgaba in a rat model of postoperative pain, Journal of Pharmacology and Experimental therapeutics, 282, 1242–1246 (1997).

Handley, S.L. and Singh, L. (1984). The effect of beta adrenoceptor agonists and antagonists on head–twitch in male mice. *Br. J. Pharmacol.*, 81, 127P.

Handley, S.L., and Singh, L. (1984). GABA modulates the head–twitch induced by L–5–HTP. *Br. J. Pharmacol.*, 82, 340P.

Handley, S.L., and Singh, L. (1986). GABAa agonists potentiate and baclofen antogonises the L–5–HTP head–twitch. *Br. J. Pharmacol.*, 84, 86P.

Handley, S.L., Mithani, S. and Singh, L. (1985). Locus Coeruleus lesions do not affect diazepam– or alpha–adrenergic modulation of operant conflict. *Br. J. Pharmacol.*, 84, 87P.

Handley, S.L., Singh, A. and Singh, L. (1986). Ritanserin reduces morphine and clonidine withdrawl ticks. *Br. J. Pharmacol.*, 89, 647P.

Tricklebank, M.D., Pharmacology, 1987, 299–302.

Iversen, S.D., Oles, R.J., Singh, L. and Tricklebank, M.D. (1986). Involvement of the haloperidol–sensitive sigma recognition site in the behaviours induced in the rat by (+)SKF–10,047. *Br. J. Pharmacol.*, 91, 340P.

Tricklebank, M.D., Wong, E., Kemp, J., Singh, L., Rupniak, N., Woodruff, G.N., Iversen, S.D., Iversen, L.L. and Watjen, F. (1988). The Pharmacological profile of FG 8205, a partial agonist at the benzodiazepine receptor. *Psychopharmacol.*, 96, 28.33.07.

Singh, L., Barth, T., Rupniak, N., Tricklebank, M.D. and Iversen, S.D. (1988). The tolerance and dependance potential of FG 8205, a partial agonist at the benzodiazepine receptor. *Psychopharmacol.*, 96, 28.33.08.

Iversen, S.D., Singh, L., Oles, R.J. and Tricklebank, M.D. (1988). The behavioural effects of excitatory amino acid (EAA) antagonists. *Psychopharmacol.*, 96, 530/112.

Tricklebank, M.D., Oles, R.J. and Singh, L. (1990). Reversal by inositol of the proconvulsant action of lithium in pilocarpine–treated mice. *Br. J. Pharmacol.*, 99, 73P.

Oles, R.J., Singh, L. and Tricklebank, M.D. (1990). Differential effects on the behavioural and anticonvulsant properties of MK–801 following repeated administration in the mouse. *Br. J. Pharmacol.*, 99, 286P.

Singh, L., Oles, R. and Woodruff, G.N. (1990). In vivo interaction of polyamine with the NMDA receptor. 20th Annual meeting Soc. for Neurosciences. St. Louis, U.S.A., 200.4.

Oles, R., Singh, L., Hughes, J. and Woodruff, G.N. (1990). The anticonvulsant action of gabapentin involves the glycine/NMDA receptor. 20th Annual meeting Soc. for Neurosciences. St. Louis, U.S.A., 221.6.

Singh, L., Field, M.J., Hughes, J., Vass, C.A. and Woodruff, G.N. (1991). Central administration of a CCK–B receptor agonist induces anxiety. *Br. J. Pharmacol.*, 102, 45P.

Field, M.J., Hughes, J., Lewis., A.S., Oles, R.J., Singh, L., Vass, C.A and Woodruff, G.N. (1991). The anxiolytic–like actions of the selective CCK–B receptor antagonist CI–988. *Br. J. Pharmacol.*, 102, 256P.

Field, M.J., Lewis, A.S., Lloyd, S. and Singh, L. (1991). Automation of the rat elevated X–maze test of anxiety. *Br. J. Pharmacol.*, 102, 304P.

Saywell, K., Singh, L., Oles, R.J., Vass, C., Leeson, P.D., Williams, B.J. and Tricklebank, M.D. (1991). The anticonvulsant properties in the mouse of the glycine/NMDA receptor antagonist, L–687,414. *Br. J. Pharmacol.*, 102, 66P.

Singh, L., Oles, R.J. and Woodruff, G.N. (1991). The lack of sedative properties of CI–988, a selective $CCK_B$ receptor antagonist. 21st Annual Meeting Soc. For Neurosciences. New Orleans, U.S.A.

Singh, L., Hughes, J., Field, M. and Woodruff, G.N.,(1992). The effects of the $CCK_B$ receptor–antagonist CI–988, on withdrawal from chronic alchol treatment. CPDD Meeting in Colorado, Jun. 20–25, 1992.

Singh, L., Field, M. and Woodruff, G.N. (1992). Selective $CCK_B$ but not $CCK_A$ receptor antagonists show anxiolytic–like action in the rat. British Association for Psychopharmacology Meeting in Cambridge, U.K., Aug. 2–7, 1992.

Field, M.J., Day, H., Vass, C.A and Woodruff, G.N. (1992). Antagonism of alchol withdrawl effects by the selective $CCK_B$ receptor antagonist CI–988. British Association for Psychopharmacology Meeting in Cambridge, U.K., Aug. 2–7, 1992.

Hargreaves K, Dubner R, Brown F, Flores C. Joris J: A new and sensitive method for measuring thermal nociception in cutaneous hyperalgesia. Pain 32: 77–88, 1988.

Woolf, CJ: Evidence for a central component of post–injury pain hypersensitivity. Nature 306: 686–688, 1983.

Treede RD, Davis KD, Campbell JN, Raja SN: The plasticity of cutaneous hyperalgesia during sympathetic ganglion blockade in patients with neuropathic pain. Brain 115 (Pt. 2): 607–621, 1992.

Woolf CJ: The pathophsiology of peripheral neuropathic pain—Abnormal peripheral input and abnormal central processing. Acta Neurochirurgica 58: 125–130, 1993.

Qian J. Brown SD, Carlton SM: Systemic ketamine attenuates nociceptive behaviors in a rat model of peripheral neuropathy. Brain Res 715: 51–62, 1996.

Coderre TJ, Melzack R: The role of NMDA receptor–operated calcium channels in persistent nociception after formalin–induced tissue injury. J Neurosci. 12:3671–3675, 1992.

Coderre TJ Melzack R: The contribution of excitory amino acids to central sensitization and peristent nociception after formalin–induced tissue injury. J Neurosci. 12: 3665–3670, 1992.

Coderre TJ, Yashpal K: Intracellular messengers contributing to persistent nociception and hyperalgesia induced by L–glutamate and substance P in the rat formalin pain model. The European Journal of Neuroscience 6: 1328–1334, 1994.

Xu XJ, Elfvin A, Wiesenfeld–Hallin Z: Subcutaneous carrageenan, but not formalin, increases the excitability of the nociceptive flexor reflex in the rat. Neuroscience Letters 196: 116–118, 1995.

McMahon SB: NGF as a mediator of inflammatory pain. Philosophical Transactions Royal Society of London 351: 431–440, 1996.

Woolf CJ: A new strategy for the treatment of inflammatory pain. Prevention or elimination of central sensitization. Drugs 47 Suppl 5: 1–9; discussion 46–47, 1994.

Woolf CJ, Chong MS: Preemptive analgesia—treating postoperative pain by preventing the establishment of central sensitization. Anesthesia and Analgesia 77: 362–379, 1993.

Sorensen J, Bengtsson A, Backman E, Henriksson KG, Bengtsson M: Pain analysis in patients with fibromyalgia. Effects of intravenous morphine, lidocaine, and ketamine. Scandinavian Journal of Rheumatology 24: 360–365, 1995.

Cavanaugh JM: Neural mechanisms of lumbar pain. Spine 20: 1804–1809, 1995.

Seibert K, Zhang Y, Leahy K, Hauser S, Masferrer J, Perkins W, Lee L, Isakson P: Pharmacological and biochemical demonstration of the role of cyclooxygenase 2 in inflammation and pain. Proceedings of the National Academy of Sciences USA 91: 12013–12017, 1994.

Sosnowski M., Pain Management: physiopathology, future research and endpoints. Support Care in Cancer 1:79–88, 1993.

Dubuisson D., Dennis, SG. The formalin test: A quantitative study of the analgesic effects of morphine, meperidine, and brain stem stimulation in rats and cats. Pain 1977; 4: 161–74.

Wheeler–Aceto H., Cowan A. Standarization of the rat paw formalin test for the evaluation of analgesics. Psychopharmacology 1991; 104: 35–44.

Kayser V., Guilbaud G. Local and remote modifications of nociceptive sensitivity during carrageenan–induced inflammation in the rat. Pain 1987; 28: 99–107.

Randall L., Selitto J. A method for measurement of analgesic activity on inflamed tissue. Arch Int. Pharmacodyn, 1957; 111: 409–19.

Brennan TJ, Vandermeulen EP, Gebhart GF. Characterization of a rat model of incisional pain. Pain 1996; 64: 493–501.

Levine JD, Fields HL, Basbaum AI. Peptides and the primary afferent nociceptor. J. Neurosci. 1993; 2273–86.

Ueda M., Kuraishi Y., Sugimoto K., Satoh M. Evidence that glutamate is released from capsaicin–sensitive primary afferent fibers in rats: Study with on–line continuous monitoring of glutamate. Neurosci. Res. 1994; 20: 231–7.

Yaksh TL, Rudy TA. Chronic catheterization of the spinal subarachnoid space. Physiol. & Behav. 1976; 17: 1031–6.

Ochoa JL, Yarnitsky D. Mechanical hyperalgesias in neuropathic pain patients; dynamic and static subtypes. Ann. Neurol 1993; 465–72.

Calcutt NA, Jorge MC, Yaksh TL, Chaplan SR. Tactile allodynia and formalin hyperalgesia in streptozocin–diabetic rats: Effects of insulin, aldose reductase inhibition and lidocaine. Pain 1996; 68: 293–9.

Bennett GJ, Xie Y–K. A peripheral monooneuropathy in rat that produces disorders of pain sensation like those seen in man. Pain 1988; 33: 87–107.

Kim SH, Chung JM. An experimental model of peripheral neuropathy produced by segmented spinal nerve ligation. Pain 1992; 50: 355–63.

Wooley, PH. Collagen–induced arthritis in the mouse. Methods in Enzymology 1988; 162: 361–373.

Holmdahl R., Tarkowski A., Jonsson R. Involvement of macrophages and dendritic cells in synovial inflammation of collagen induced arthritis in DBA/1 mice and spontaneous arthritis in MRL/Lpr mice. Autoimmunity 1991; 8: 271–280.

Hill DR, Suman–Chauhan N., Woodruff GN. Localization of [3H]–gabapentin to a novel site in rat brain: Autoradiographic studies. Eur. J. Pharmacol. 1993; 244: 303–9.

Kocsis JD, Honmou O. Gabapentin increases GABA–induced depolarization in rat neonatal optic nerve. Neuroscience Letters 1994; 169: 181–4.
Ragsdale DS, Scheuer T., Catterall WA. Frequency and voltage–dependent inhibition of type IIA Na+ expressed in a mammalian cell line, by local anesthetic, antiarrhythmic, and anticonvulsant drugs. Molec. Pharmacol. 1991; 40: 756–65.
Moertel, et al., "Relief of Pain by Oral Medications," Analgesic Combinations, vol. 229, No. 1, Jul. 1, 1974.
Sawynok, Jana, "GABAergic Mechanisms of Analgesia: An Update," Pharmacology Biochemistry and Behavior, vol. 26, pp. 463–474 (1987).
Visceral Pain: a review of experimental studies, Pain 41: 167–234, 1990.
Mayer & Raybould, Role of Visceral Afferent Mechanisms in Functional Bowel Disorders, Gastroenterology 1990 89:1688–1704.
Mayer & Gebhart, Basic and Clinical Aspects of Visceral Hyperalgesia, Gastroenterology 1994: 107: 271–293.
Miampamba, et al., "Inflammation of the colonic wall induced by formalin as a model of acute visceral pain," Pain 57 (1994) 327–334.
Morteau, et al., "Experimental Colitis Alters Visceromotol Response to Colorectal Distension in Awake Rats, " Digestive Diseases and Sciences, vol. 39, No. 6 (Jun. 1994); pp. 1239–1248.
Lever et al., Annual Reports in Medicinal Chemistry (vol. 19), p. 5, 1984.
Berge et al., J. Pharm. Sci., 66:1–9, 1977.
Taylor, Mechanisms of analgesia by gabapentin and pregabalin—Calcium channel α2–σ [$Ca_v$α2–σ]ligands, Pain 142 (2009) 13–16.
Xiao et al., Analgesia 2:267–273, 1996 (with cover page).
Prescribing Information for Lyrica®.
Allinger et al., *Organic Chemistry*, Chapter 6, Worth Publishers. Inc., 1971.
March, J. *Advanced Organic chemistry; Reactions, Mechanisms and Structure*, McGraw–Hill Book Company, 1968.
Morrison, *Asymmetric Synthesis*, vol. 1.1. Academic Press, 1983, Chapter 6 (Pirkle and Finn).
Witczuk et al., (1978)*3–(p–tolyl)–4–aminobutanoic acid, synthesis, resolution into enantiomers and pharmacological activity*. Pol. J. Pharmacol. Pharmacological activity. Pol. J. Pharmacol. Pharm. 30:95–103 ("Witczuk 1978").
Witczuk B et al. (1980) *3–(p–chlorophenyl)–4–aminobutanoic acid—resolution into enantiomers and pharmacological activity*. Pol. J. Pharmacol. Pharm. 32:187–196 ("Witczuk 1980").
Eliel, Ernest L., *Sterchemistry of Chemical Compounds*, International Student Edition., (McGraw Book Company Inc., 1962).
March, J., *Advanced Organic Chemistry*, 3rd Edition, John Wiley & Sons, 1985; Enantiomers, Racemates and Resolutions (J. Jacques et al. eds.) pp. 378–379 (1981).
Norman, RO.C, *Principles of Organic Synthesis*, (Methuen Co., Ltd., 1968).
Jacques, J. Collet, A., and Wilen, S.H. *Enantiomers, Racemates and Resolutions*, Wiley, New York 1981.
ten Hoeve, W. and Wynberg, *The Design of Resolving Agents: Chiral Cyclic Phosphoric Acids*. H.J. Org. Chem. 1985, 50, 4508.
S.H. Wilen, *Tables of Resolving Agents and Optical resolutions*, University of Notre Dame Press, 1972.
Martens J. and Bhushan R. *T.I.C. enantiomeric seperation of amino acids*. Int. J. Pept. Protein Res. Dec. 1989; 34(6)433–44, ("Martens 1989").
Maurs M. et al., (1988) *Resolution of alpha–substituted amino acid enantiomers by high–performance liquid chromatography after derivitization with a chiral adduct of o–pthalaldehyde*. Application to glutamic acid analogues. J. Chromatogr. 25; 440:209–215 ("Maurs 1988").
Hare PE. (1988) *Chiral Mobile Phases for the Enantiomeric Resolution of Amino Acids*. Chromatographic Chiral Separations. (eds. Zief M. and Crane LJ.).
Wainer, Trends in Analytical Chemistry, 6, 125–134 (1987).
Railton, J. Chromatography, 402,371–373 (1987).
Johns, American Laboratory, 72–76 (Jan. 1987).
AM. Krstulovic, J. Pharm. & Biomed. Analysis, Sep. 1987.
AM. Krstulovic, J. Pharm. & Biomed. Analysis, 6(6–8), 1988, 641–656.
D. W. Armstrong, Anal Chem. 59(2), 1987, 84A–91A.
Hermansson, J. Chromatogr, 269, 1983, 71–80.
Chiralpak Chiralcel HPLC columns advertisement. J. Chromatogr., 450, No. 2., 1988; 205c.
Hermansson, J., *Resolution of Racemic Aminoalcohols({3–Blockers), Amines and Acids as Enantiomeric Derivatives Using a Chiral a1–Acid Glycoprotein Column:*, J. Chromatogr., 325, 379–384 (1985).
Hermansson, J., et al. *Direct Liquid Chromatographic Resolution of Acidic Drugs Using a Chiral a1–Acid–Glycoprotein Column(Enantiopac)*, J. Liq. Chromatogr., 9 (2&3), (1986) 621–639.
Wainer Barkan and Schill, LC–GC 4(5), (1986) 422–430.
Schill, Wainer and Barkan, J. Chromatogr., 365 (1986) 73–88.
Debowksi, Sybilska, and Jurczak, J. Chromatogr. 237 (1982) 303–306; Bopp and Kennedy, LC–GC 6(6), 1988 514–522.
Bopp and Kennedy, LC–GC 6(6), (1988) 514–522.
Beesley, American Laboratory (May, 1985), 78–87.
Okamoto, Kawashima, and Hatada, J. Chromatogr. 363 (1986) 173–186.
Armstrong and DeMond, J. Chromatogr. Sci. 22 (1984) 411–415.
Schill, Wainer and Barkan, J. Liq. Chromatogr., 9(2&3), (1986) 641–666.
J.T. Baker Advertisements for chiral columns, 1986 and 1988.
Excerpts from J.T. Baker Catalog 870C; Chiralcel OD advertisement, C&EN, Jun. 20, 1988.
J.T. Baker advertisement, LC.GC 4(10), Oct. 1986.
Regis advertisement, LC.GC 4(4) Apr. 1986,
Prochrom preparative HPLC advertisements LC.GC, 5(5) Aug. 1987 and LC.GC, 6(2) Feb, 1988.
Sepragen preparative HPLC advertisements LC.GC 4(6) Jun. 1986.
Allan RD, et al. (1990) *A New Synthesis, Resolution and in vitro Activities of(R)– and (S)–f3–phenylGABA*. Tetrahedron 46(7): 2511–24 Allan 1990).
Olpe H, et al., *Eur. J. Pharmacol* 1978, 52, 133–136.
Belokon YN et al., (1986) *Synthesis of Enantio– and Diastero–isomerically Pure β– and y–Substituted Glutamic Acids via Glycine Condensation with Activated Olefins*. J. Chem. Soc. Perkin Trans. 1:1865–1872.
Takano S. et al., (1987) *Fractional Synthesis of (R)–y–amino– β–hydroxybutanoic acid (GABOB) from (R)–epichlorohydrin*, Tetrahedron Letters 28(16): 1783–1784.

Thaisrivongs S. et al., *Renin Inhibitors*, J. Med. Chem. 1987, 30, 976–982.

Fadel A. and Salaun J (1988) *Optically Active α–alkylsuccinates from the stereoselective alkylation of chiral imide enolates*. Tetrahedron Letters 29(48): 6257–6260.

Fromm GH and Terrence CF (1987) *Comparison of L–baclofen and racemic baclofen in trigeminal neuralgia*. Neurology 37: 1725–1728 ("Fromm 1987").

Hill DR et al. (1993) *Localization of [3H ]gabapentin to a novel site in rat brain: autoradiographic studies*. European Journal of Pharmacology 244(3):303–309.

Allan RD et al. (1990) *A New Synthesis, Resolution and in vitro Activities of(R)and (S)–(β–phenyl–GABA*. Tetrahedron 46(7):2511–2524 ("Allan 1990").

Weiner RS (2002) *Pain Management: A Practical Guide for Clinicians* (6th ed.) ("Weiner 2002").

Xiao WH and Bennett GJ (1995) *Synthetic w–Conopeptides Applied to the Site of Nerve Injury Suppress Neuropathic Pains in Rats*, Journal of Pharmacology and Experimental Therapeutics 274(2):666–672.

Lapin IP et al. (1986) *Antagonism of Seizures Induced by the Administration of the Endogenous Convulsant Quinolinic Acid into RatBrain Ventricles*, J. Neural Transmission 65:177–185.

Benedito MA and Leite JR (1981) *Baclofen as an Anticonvulsant in Experimental Models of Convulsions*, Experimental Neurology 72:346–351.

Sawynok J. (1984) *gabaergic Mechanisms in Antinociception, Prog. Neuro–Psychopharmacol.& Biol. Psychiat.* 8:581–586 at p. 583–584.

Vaught JL et al. (1985) *A Comparison of the Antinociceptive Responses to the GABA–Receptor Agonists THIP and Baclofen*, Neuropharmacology 24(3):211–216.

Zarrindast MR and Djavadan M (1988) *$GABA_A$–Antagonists and Baclofen Analgesia*, Gen Pharmac. 19(5):703–706.

Bucklett WR (1980) *Irreversible Inhibitors of GABA Transaminase Induce Antinociceptive Effects and Potentiate Morphine*, Neuropharmacology 19:715–722.

Sawynok J and Dickson C (1983) *Involvement of GABA in the Antinociceptive Effect of y–acetylic GABA(GAG), an Inhibitor of GABA–Transaminase*, Gen. Pharmac, 14(6):603–607.

Kendal DA et al. (1982) *Comparison of the Antinociceptive Effect of y–Aminobutyric(GABA)Agonists: Evidence for a Cholinergic Involvement*, J. Pharmacol. & Therap.220(3):482–487.

Hammond EJ and Wilder BJ (1985) *Minireview: Gamma–Vinyl GABA*Gen. Pharmac. 16(5):441–447.

Meldrum B and Horton R (1978) *Blockade of Epileptic Resonses in the Photosensitive Baboon, Papio papio, by Two Irreversible Inhibitors of GABA–Transaminase, y–Acetylic GABA (4–Aminohex–5–yonic Acid)and y–Vinyl GABA(Amino–hex–5–enoic Acid)*, Psychopharmacology 59:47–50.

Griffin et al. (1993) *Peripheral Neuropathy*, 3rd ed., ("Griffin 1993").

Presley RW. *Novel appriaches to the treatment of neuropathic pain*. West J Med. 1992 Nov.; 157(5):564.

Simon RP et al. (1989)*Clinical Neurology*, Appleton & Langel, East Norwalk, CT at p. 72.

Cherny NI, et al. [*Pharmacotherapy of cancer pain. 3. Adjuvant drugs*][*Article in German*]Schmerz. Mar. 1995; 9(2):55–69.

Hegarty A. and Portenoy RK. (1994) *Pharmacotherapy of neuropathic pain. Seminars in Neurology*, 14,213–224 (Hegarty & Portenoy, 1994).

Swerdlow, M. (1984) *Anticonvulsant drugs and chronic pain.* Clinical Neuropharmacology, 7, 51–82. (Swerdlow, 1984).

Kloke (1991) *Anti–depressants and anti–convulsants for the treatment of neuropathic pain syndromes in cancer patients*. Onkologie 14(1):40–3.

Bartusch SL et al. (1996) *Clonazepam for the treatment of lancinating phantom limb pain*. Clin J Pain. 12(1)59–62.

McQuay HJ and Moore RA, (1997) *Systematic review of outpatient services for chronic pain control, Chapter 14—Anticonvulsant Drugs*, Health Technology Assessment 1997, vol. 1, No. 6: 65–74.

Nagahisa A. et al. (1992) *Non–specific activity of(±)–CP–96, 345 in models of pain and inflammation*, Br. J. Pharmacol. 107:273–275.

Winter CA et al. (1962) *Carrageenan–induced edema in hind paw of the rat as an assay for anti–inflammatory drugs*.Proceedings of the Society for Experimental Biology and Medicine 111:544–547.

Kandel, Schwartz & Jessell (1991) *Principles of Neural Science*, 3rd ed.

Dubner R, Hargreaves KM (1989) *The neurobiology of pain and its modulation*. Clin J Pain 5 Suppl. 2:S1–6.

McQuay HJ (1988) *Pharmacological treatment of neuralgic and neuropathic pain*. Cancer Surveys, 7(1): 141–159).

Elliott KJ (1994) *Taxonomy and Mechanisms of Neuropathic Pain*, Seminars in Neurology 14(3): 195–205.

Bennett GJ (1993) *An Animal Model of Neuropathic Pain: A Review*, Muscle & Nerve 16:1040–1048.

Mao J et al. (1993) *Patterns of Increased Brain Activity Indicative of Pain in a Rat Model of Peripheral Neuropathy*, The Journal of Neuroscience 13(6): 2689–2702.

Smith et al. (1994) *Increased sensitivity to the antinociceptive activity of (+/−)–baclofen in an animal model of chronic neuropathic, but not chronic inflammatory hyperalgesia*. Neuropharmacology, Sep. 1994; 33(9): 1103–8.

Merskey, H. & Bogduk, N. (1994) *Classification of chronic pain. Descriptions of chronic pain syndromes and definitions of pain terms* (2nd ed.) Seattle: IASP Press.

Bonica JJ (1990) *The Management of Pain*, 2nd ed., Lippincott Williams & Wilkins, Philadelphia.

Moote CA, *The prevention of postoperative pain*. Can J Anaesth. Jun. 1994; (6):527–33.

Bennett G.J., and Xie Y.K., Pain 1988; 33:87–107.

Kim S.H. et al., Pain 1990; 50:355–363.

McCaffery M and Pasero P (1999) *Pain: Clinical Manual* (2nd ed.), Mosby, Inc., St. Louis.

Simon RP et al., (1989) *Clinical Neurology*, Appleton & Lange, East Norwalk, CT, at chapters 3 and 7.

Dyck PJ et al. (1987) *Diabetic Neuropathy*, WB Saunders Co., Philadelphia.

Schmidt RE et al. (1981) *Experimental Diabetic Autonomic Neuropathy*, AJP 103(2): 210–225.

Houghton AD et al., *Phantom pain: natural history and association with rehabilitation* Ann R Coli Surg Engl. Jan. 1994; 76(1):22–5.

Volmink J. et al. *Treatments for postherpetic neuralgia—a systematic review of randomized controlled trials* Fam Pract. Feb. 1996; 13(1):84–91.

Bennett GJ. (1994) Hypotheses on the Pathogenesis of Herpes Zoster–associated Pain, Annals of Neurology vol. 35 (Suppl. )S38–S41.
Bowsher D. (1997) *The management of postherpetic neuralgia*, Postgrad Med J 73:623–629.
Mamdani, FS (1994) *Pharmacologic management of herpes zoster and postherpetic neuralgia*, Canadian Family Physician 40:321–332.
Wolfe F., *Fibromyalgia and myofascial pain syndrome*. In Portenoy RK, Kanner RM: Pain management: theory and practice, p. 145–169, Philadelphia, 1996, FA Davis.
Carette S., *Chronic pain syndromes*, Annals of the Rheumatic Diseases 1996; 55: 497–501.
Doherty M. and Jones A *ABC of rheumatology Fibromyalgia syndrome*. BMJ. Feb. 11, 1995; 310(6976): 386–389.
Yunus MB (1989) *Fibromyalgia syndrome: new research on an old malady*, BMJ 298:474–475.
Goldenberg DL (1995) *Fibromyalgia: why such controversy?* Annals of the Rheumatic Diseases 54:3–5.
Wade A, Weller, PJ (1994) *Handbook of Pharmaceutical Excipients*2nd ed., American Pharmaceutical Association, Academy of Pharmaceutical Sciences, Pharmaceutical Society of Great Britain.
Neurontin® Product Monograph, revised Feb. 25, 2008.
Lyrica® Product Monograph, revised Mar. 3, 2009.
Hunter JC. et al., (1997) The effect of novel anti–epileptic drugs in rat experimental models of acute and chronic pain. Eur J Pharmacol. Apr. 18, 1997;324(2–3):153–60.
Samkoff LM. et al., (1997) Amelioration of refractory dysesthetic limb pain in multiple sclerosis by gabepentin. Neurology. Jul. 1997; 49(1):304–305.
Kim, Yoon C. et al., Glutamic Acid Analogs. The Synthesis of 3–Alkylgutamic Acids and 4–Alkylpyroglutatmic Acids. J. Med. Chem. 1965, 8(4), 509–513.
Cahn, R.S. et al., Specification of Molecular Chirality. Angew. Chem. Internat. Edit. vol. 5 (1966) No. 4, 385–583.
Moss, G.P., Basic Terminology of Stereochemistry. Pure & Appl. Chem. vol. 68, No. 12, 2193–2222 (1996).
Cates, Lindley A. Calculation of Drug Solubilities by Pharmacy Students. American Journal of Pharmaceutical Education. vol. 45, Feb. 1981, 11–13.
Schechter, et al. Attempts to Correlate Alterations in Brain GABA Metabolism by GABA–T Inhibitors with their Anticonvulsant Effects. GABA–Biochemistry and CNS Functions. 43–57 (1979).
Silverman, Richard B. and Levy, Mark A. Synthesis of (S)–5–Substituted 4–Aminopentanoic Acids: A New Class of y–Aminobutyric Acid Transaminase Inactivators. J. Org. Chem. 1980, 45, 815–818.
Mathew, Jacob et al., An Efficent Synthesis of 3–Amino–4–Fluorobutanoic Acid, an Inactivator of GABA Transaminase. Synthetic Communications, 15(5), 377–383 (1985).
Silverman, Richard B. et al., Inactivation of y–Aminobutyric Acid Aminotransferase by (Z)–4–Amino–2–fluorobut–2–enoic Acid. Biochemistry 1988, 27, 3285–3289.
Prelog, Valdimir et al. Basic Principles of the CIP–System and Proposals for a Revision, Angew. Chem. Int. Ed. Engl. 21 (1982) 567–583.
Field, et al. Detection of static and dynamic components of mechanical allodynia in rat models of neuropathic pain: are they signaled by distinct primary sensory neurons? Pain 83 (1990), 303–311.
Van, Jon, "Drug Find Worth $700 Million But Chemist Finds It a Tough Sell to Turn Over Project," Chicago Tribune, Mar. 10, 2008.
Silverman, Richard B. From Basic Science to Blockbuster Drug: The Discovery of Lyrica. Angew. Chem. Int. Ed. 2008, 47, 3500–3504.
Defeudis, "Central GABA–ergic Systems and Analgesia", Drug Dev. Res., 3, pp. 1–15, 1983.
Harrison, "Modulation of the GABA Receptor Complex by a Steroid Anaesthetic", Brain Res., 323, pp. 287–292, 1984.
Krogsgaard–Larsen, "Heterocyclic Analogues of GABA: Chemistry, Molecular Pharmacology and Therapeutic Areas", Progress in Medicinal Chemistry, 22, pp. 67–120, 1985.
Hernandez, et al., "A Substrate for GABA–ergic Modulation of Dental Pulp Nociceptive Transmission", J. Dental Res., 65 (Spec. Issue), p. 754, 1986.
Andruskiewicz, et al., "A Convenient Synthesis of 3–Alkyl–4–aminobutanoic Acids", Synthesis, pp. 953–955, Dec. 1989.
Andruszkiewicz, et al., "4–Amino–3–Alkylbutanoic Acids as Substrates for Gamma–Aminobutyric Acid Aminotransferase", Journal of Biological Chemistry, 265 (36), 22288–91, 1990.
Silverman, et al., "3–Alkyl–4–aminobutyric Acids: The First Class of Anticonvulsant Agents That Activates L–Glutamic Acid Decarboxylase", J. Med. Chem., 34, p. 2295–98, 1991.
Johnston, "GABAA Agonists as Targets for Drug Development", Clin. Exp. Pharmacol. and Physiol., 19, pp. 73–78, 1992.
Taylor, et al., "Pharmacology of Gabapentin, a Novel Anticonvulsant, In Vitro and in Experimental Animals", J. Epilepsia, 33 (Suppl. 3), p. 117, 1992.
Pfeifer, et al., "A Highly Successful and Novel Model for Treatment of Chronic Painful Diabetic Peripheral Neuropathy", Diabetes Care, 16 (8), pp. 1103–1115, 1993.
Suman–Chauhan, et al., "Characterisation of [3H]Gabapentin Binding to a Novel Site in Rat Brain:Homogenate Binding Studies", Eur. J. Pharmacol., 244 (3), pp. 293–301, 1993.
Taylor, "Mechanism of Action of New Anti–Epileptic Drugs", Royal Society of Medicine Inter.l Congress and Symposium Series New Trends in Epilepsy Management, 198, p. 13–40, 1993.
Taylor, et al., Potent and Stereospecific Anticonvulsant Activity of 3–Isobutyl GABA Relates to in Vitro at a Novel Site Labeled by . . . Epilepsy Res., p. 11–15, 1993.
Thurlow, et al., "[3H]Gabapentin May Label a System–L––Like Neutral Amino Acid Carrier in Brain", European Journal of Pharmacology, 247, pp. 341–345, 1993.
Krogsgaard, et al., "GABAA Receptor Agonists, Partial Agonists and Antagonists. Design and Therapeutic Prospects", J. Med. Chem., 37(16), pp. 2489–2505, 1994.
Taylor, "Perspectives on the Pharmacology of Gabapentin (Neurontin) and Potential Mechanism of Action", Boll. Lega. It. Epii. 86/87, pp. 51–53, 1994.
Taylor, "Emerging Perspective on the Mechanism of Action of Gabapentin", Neurology, 44 (Suppl. 5), pp. S10–S16, 1994.
Davies, "Mechanisms of Action of Antiepileptic Drugs", Seizure, 4, pp. 267–271, 1995.
Galer, "Neuropathic pain of Peripheral Origin: Advances in Pharmacologic Treatment", Neurology, 45 (Suppl. 9), pp. S17–S25, 1995.

Radulovic, et al.; "The Preclinical Pharmacology, Pharmacokinetics and Toxicology of Gabapentin"; Drugs of Today, 31 (8), pp. 597–611, 1995.
Taylor, "Gabapentin: Mechanisms of Action", Antiepileptic Drugs (Fourth Edition), pp. 829–841, 1995.
Wang, et al., "Pharmacokinetic and Pharmacodynamic Comparison of Two Anticonvulsant Compounds, Gabapentin and Isobutyl GABA",J. Pharmaceutical Research, 12(Suppl. 9), p. S400 1995.
Xiao, et al. Gabapentin Relieves Abnormal Pains in a Rat Model of Painful Peripheral Neuropathy, Soc. For Neuroscience Abstracts, 21, p. 897, 1995.
Gilron, et al., "Preemptive Analgesic Effects of Steroid Anesthesia with Aphaxalone in the Rat Formalin Test", Anesthesiology, 84 (3), pp. 572–579, 1996.
Hill, "Meeting Highlights Central & Peripheral Nervous Systems ( Butt 8th World Pain Congress)", Expert Opinion Invest. Drugs, 5(11), pp. 1549–1562, 1996.
Mathew, et al., "Gabapentin in Migraine Prophylaxis: A Preliminary Open Label Study", Neurology, 46 (Suppl. 2), p. A169, 1996.
Schachter, et al., "Treatment of Central Pain with Gabapentin: Case reports", J. of Epilepsy, 9(3), pp. 223–226, 1996.
Shimoyama, et al., "Spinal Gabapentin is Antinoceptive in the Rat Formalin Test", Society for Neuroscience Abstracts, 22, p. 1371, 1996.
Singh, et al., "The Antiepileptic Agent Gabapentin Posseses Anxiolytic–Like and Antinociceptive Actions that are Reversed by D–Serine", Psychopharmacology, 127, pp. 1–9, 1996.
Stacey, et al., "Gabapentin and Neuropathic Pain States: A Case Series Report", Regional Anesthesia, 21 (Suppl. 2), p. 65, 1996.
Vinik, et al., "Recent Advances in the Diagnosis and Treatment of Diabetic Neuropathy", Endocrinologist, 6 (6), pp. 443–461, 1996.
Xiao, et al., "Gabapentin Has an Antinociceptive Effect Mediated via a Spinal Site of Action in a Rat Model of Painful Peripheral Neuropathy", Analgesia, 2, pp. 267–273, 1996.
Field, et al., "Gabapentin (Neurontin) and S–(+)–3–Isobutylgaba Represent a Novel Class of Selective Antihyperalgesic Agents", Br. J. Parmacol., 121, pp. 1513–1522, 1997.
Field, et al., "Evaluation of Gabapentin and S–(+)–3–Isobutylgaba in a Rat Model of Postoperative Pain", J. Pharmacol. Exp. Ther., 282 (3), pp. 1242–1246, 1997.
Bryans, et al., "Gabapentin SAR–Towards Novel Treatments for Pain", Abstracts of Papers American Chemical Society, 216(1), p. MEDI 207, 1998.
Bryans, et al., "Identification of Novel Ligands for the Gabapentin Binding Site on the α2σ Subunit of a Calcium Channel and . . . ", J. Med. Chem., 41, p1838–45, 1998.
Partridge, et al, "characterization of the Effects of Gabapentin and 3–Isobutyl–y–Aminobutyric Acid on Substance P–induced. . .", Anesthesiology, 88 (1), p196–205, 1998.
Taylor, et al., "A Summary of Mechanistic Hypothesis of Gabapentin Pharmacology", Epilepsy Research, 29, pp. 233–249, 1998.
Field, et al., "Gabapentin and Pregabalin, but not Morphine and Amitriptyline, Block Both Static and Dynamic Components of Mechanical . . . ", Pain (Neth.), 80, p391–98, Mar. 1999.
Field, et al., "The Gabapentin Analogue 3–Methyl–Gabapentin Blocks Both Static and Dynamic Components of Mechanical Allodynia in . . . ", British J. of Pharm., 128, p235P, 1999.
Field, et al., "Detection of Static and Dynamic Components of Mechanical Allodynia in Rat Models of NeuropathicPain: Are They Signalled by . . . ", 83, p303–11, 1999.
Blakemore, et al., "Gabapentin SAR: Toward Novel Treatment for Pain", Abstracts of Papers Americna Chemical Society, 220 (Part 1), p. MEDI 239, 2000.
Field, et al., "Futher Evidence for the Role of the α2σ Subunit of Voltage Dependent Calcium Channels in Models of NeuropathicPain", Br. J. of Pharm., 131 (2), p282–86, 2000.
Laird, et al., "Use of Gabapentin in the Treatment of Neuropathic Pain", Annals of Pharmacotherapy, 34, pp. 802–807, 2000.
Buirkle, et al., "Pregabalin Inhibits Mechanical Hyperalgesia Origination in the Musculoskeletal System", J. Society for Neuroscience Abstracts, 27(1), p. 1332, 2001.
Taylor, et al., "Pregabalin Inhibits Multiple Endpoints of Carrageenan Induced Pain but Not Inflammation in Rats", J. Society for Neuroscience Abstracts, 27(2), p. 1897, 2001.
Rose, et al., "Gabapentin: Pharmacology and Its Use in Pain Management", Anaesthesia, 57, pp. 451–462, 2002.
Bellioti, et al., "Structure–Activity Relationships of Pregabalin and Analogues that Target the α2σ Protein", J. Med. Chem, 48 (7), pp. 2294–2307, 2005.
Bian, et al., "Calcium Channel Alpha2–Delta Type 1 Subunit is the Major Binding Protein for Pregabalin in Neocortex, Hippocampus, . . . ", Brain Research, 1075, p. 68–80, 2006.
Rogawski, et al., "Calcium α2–σ Subunit, A New Antiepileptic Drug Target", Epilepsy Res., 69(3), pp. 183–272, 2006.
Vartanian, et al., "Activity Profile of Pregabalin in Rodent Models of Epilepsy and Ataxia", Epilepsy Res., 68, pp. 189–205, 2006.
Taylor, et al, "Pharmacology and Mechanism of Action of Pregablin: The Calcium Channel α2–σ (Alpha2–Delta) Subunit as a Target . . . ", Epilepsy Res., 73, p. 137–50, 2007.
Yuen et al., Enantioselective Synthesis of PD144723: A Potent Stereospecific Anticonvulsant, Bioorg. Medicinal Chemistry Letters, 4 (6), pp. 823–826, 1994.
Lyrica U.S. Physician Prescribing Information.
Neurontin U.S. Physician Prescribing Information.
EP 0934061 File History (including Opposition Document)s.
CA 2,255,652 File History (including Application for Reissue filed Dec. 20, 2005).
Apr. 14, 2005 Declaration of Charles Taylor submitted in Japanese Application No. JP507062/98.
Translation of Written Opinion of ANVISA refusing to consent to grant of patent based on allowed Brazillian Patent Application No. P19710536–8.

* cited by examiner

FIG-1a GABAPENTIN
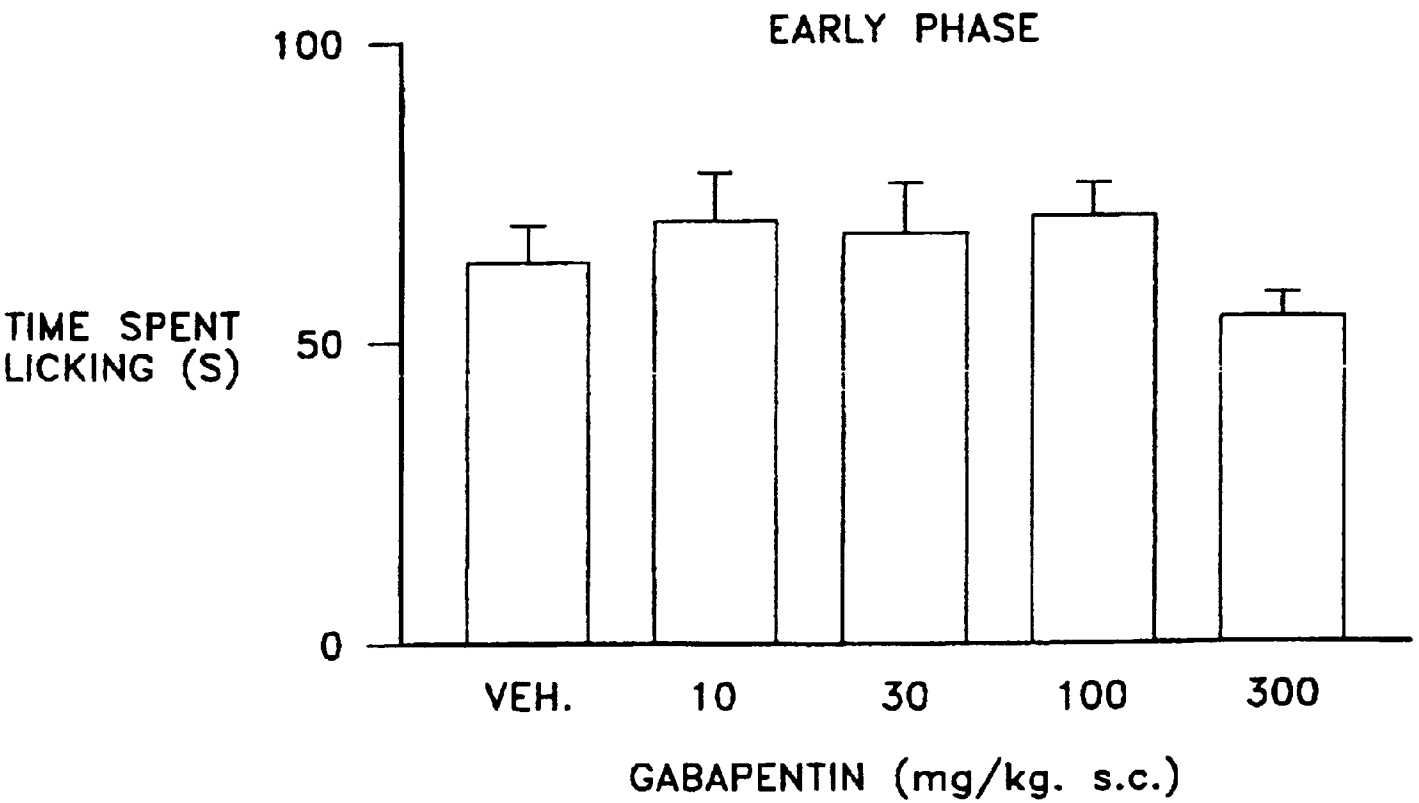

FIG-1b GABAPENTIN
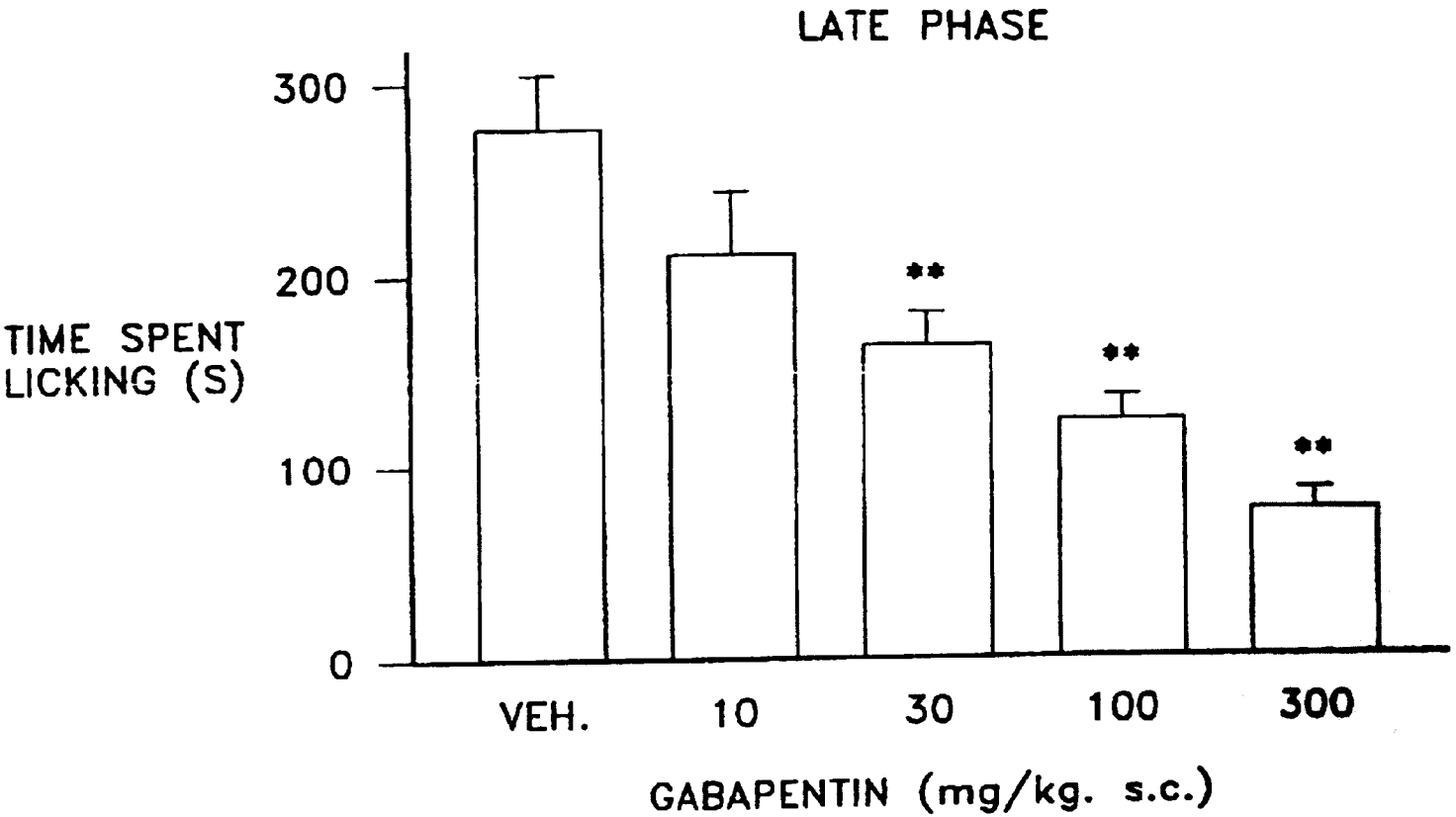

FIG-1c CI-1008
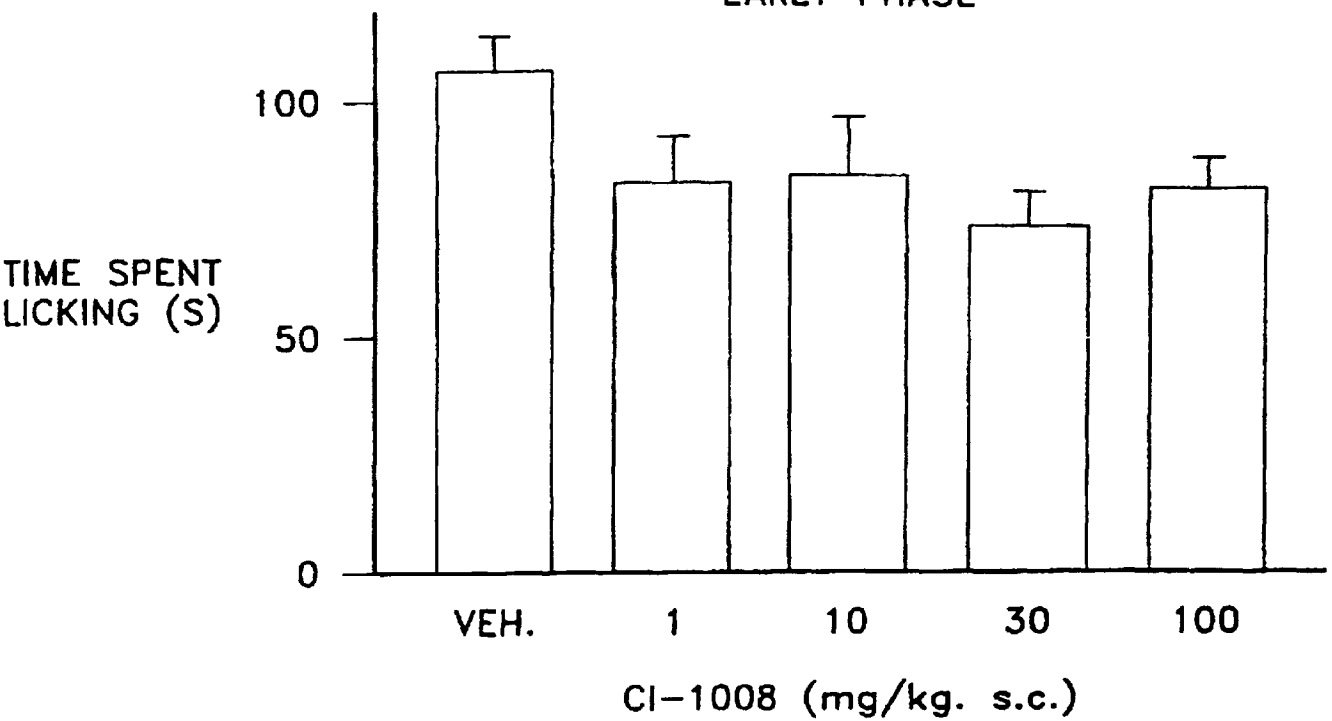

FIG-1d CI-1008
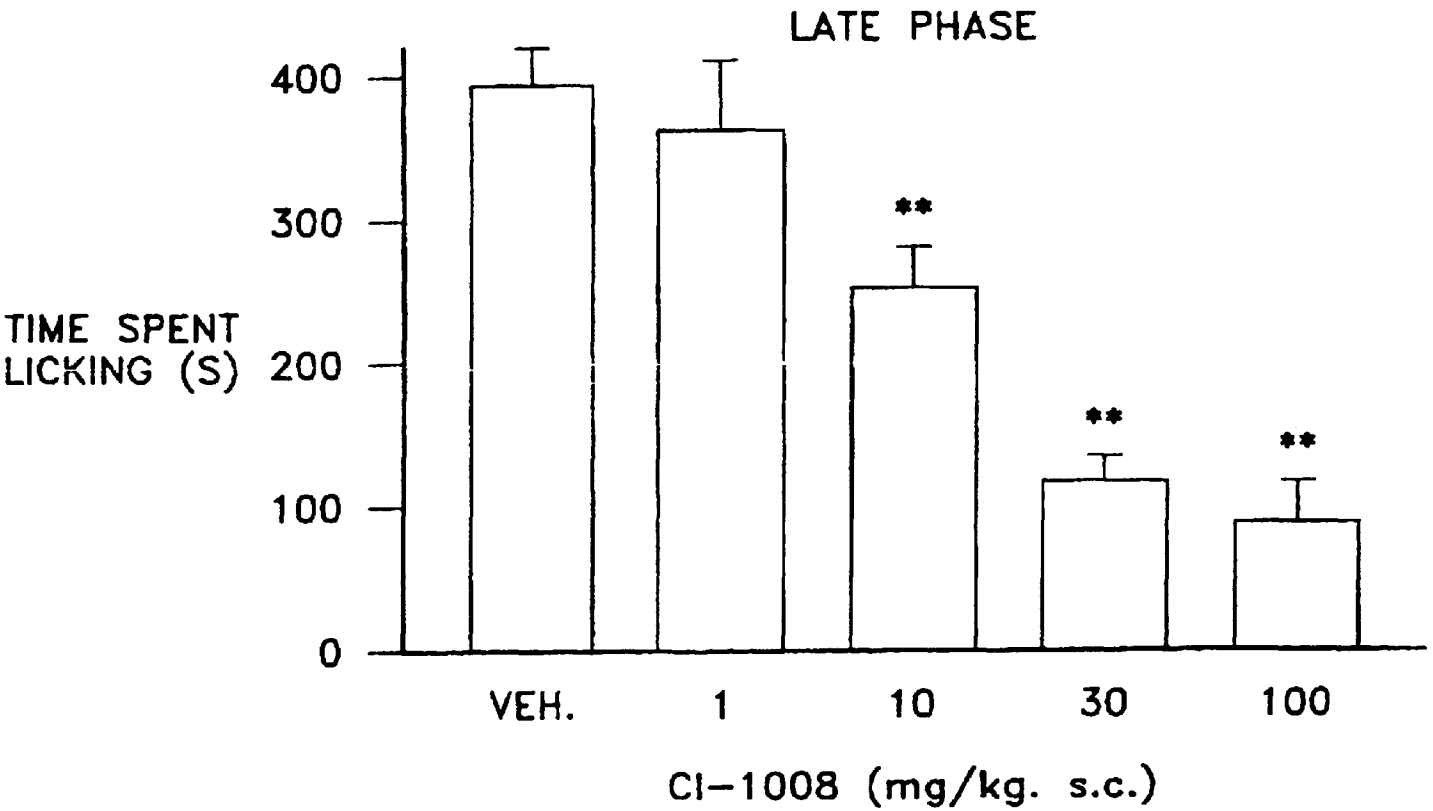

FIG-1e PD 144550
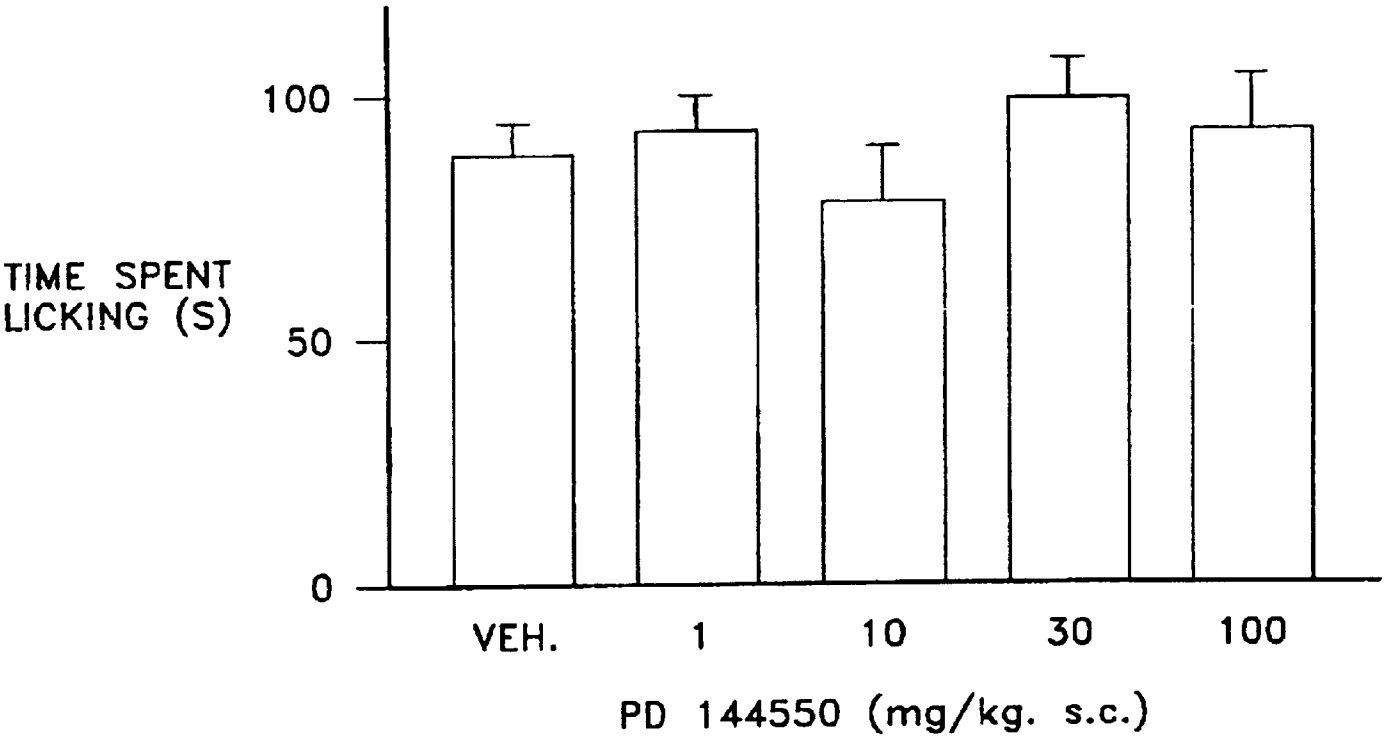

FIG-1f PD 144550
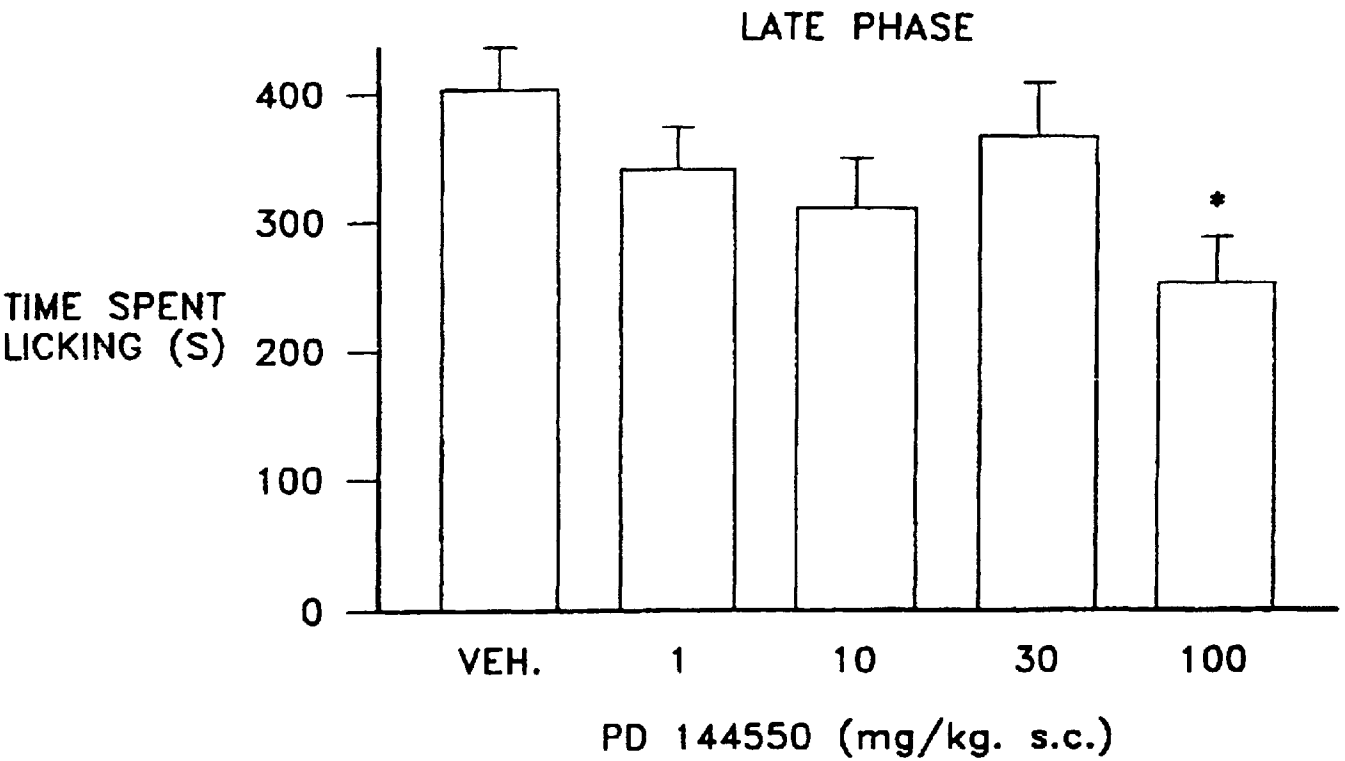

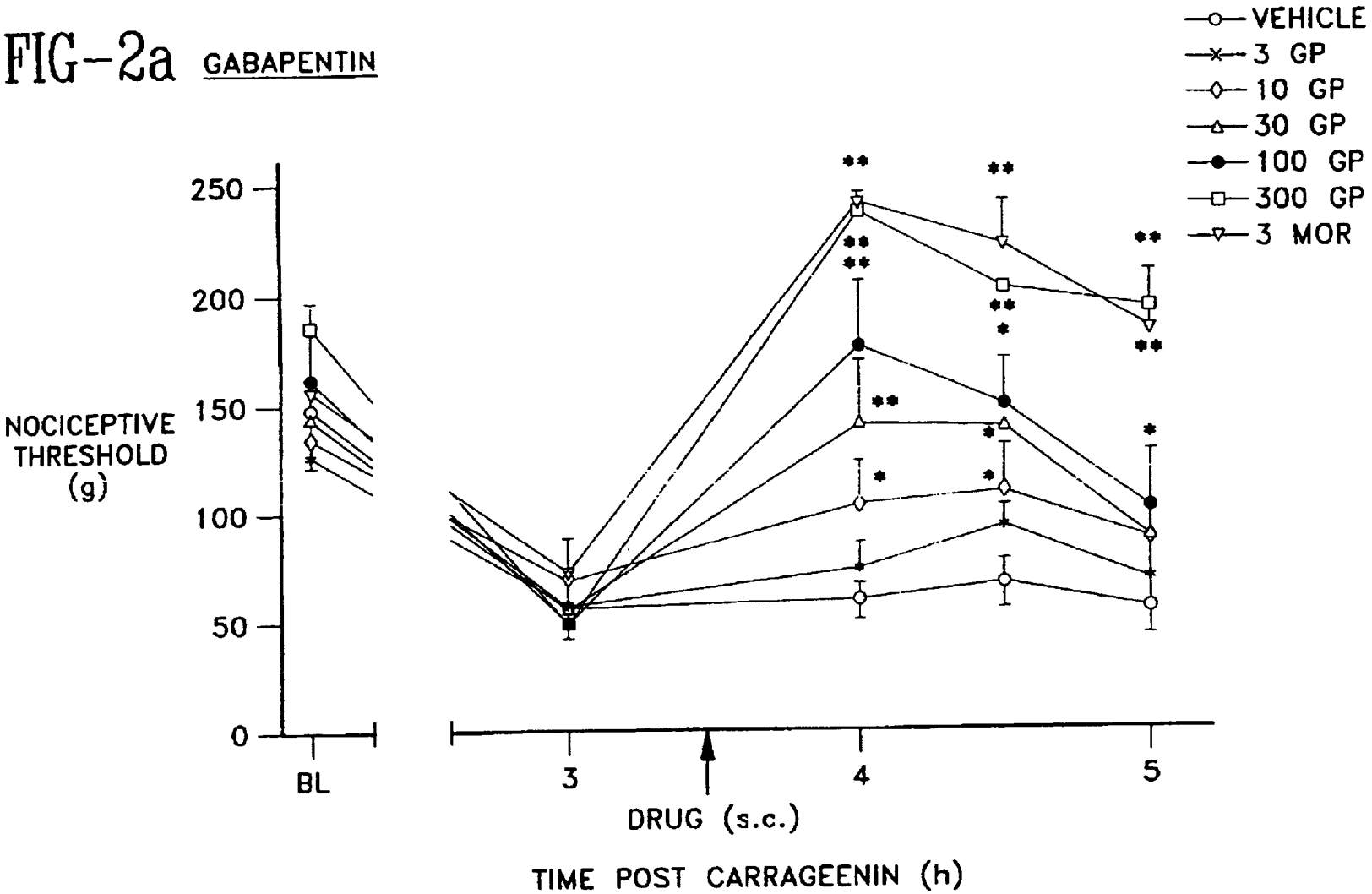
FIG-2a GABAPENTIN

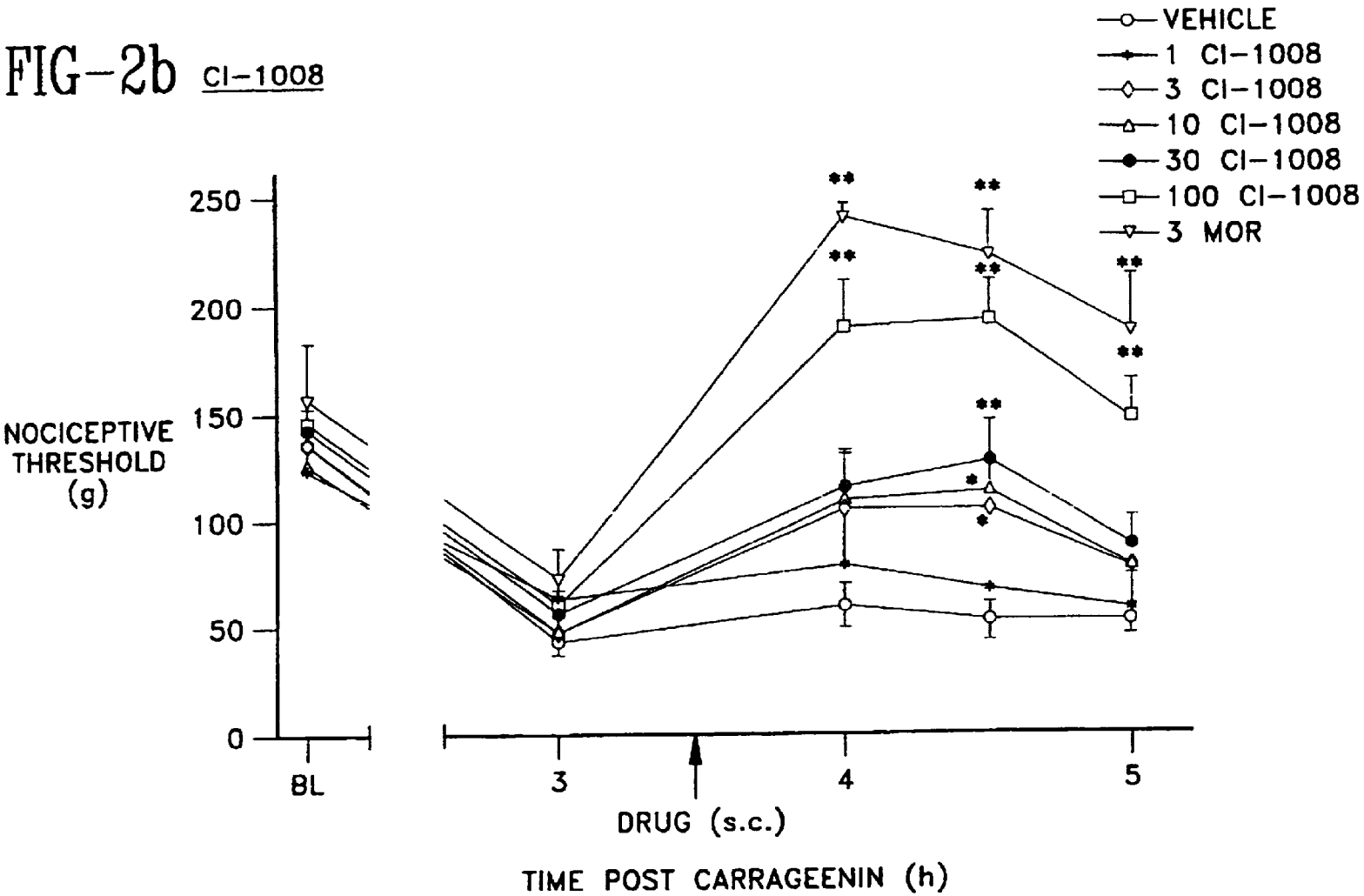
FIG-2b CI-1008

FIG-3a GABAPENTIN
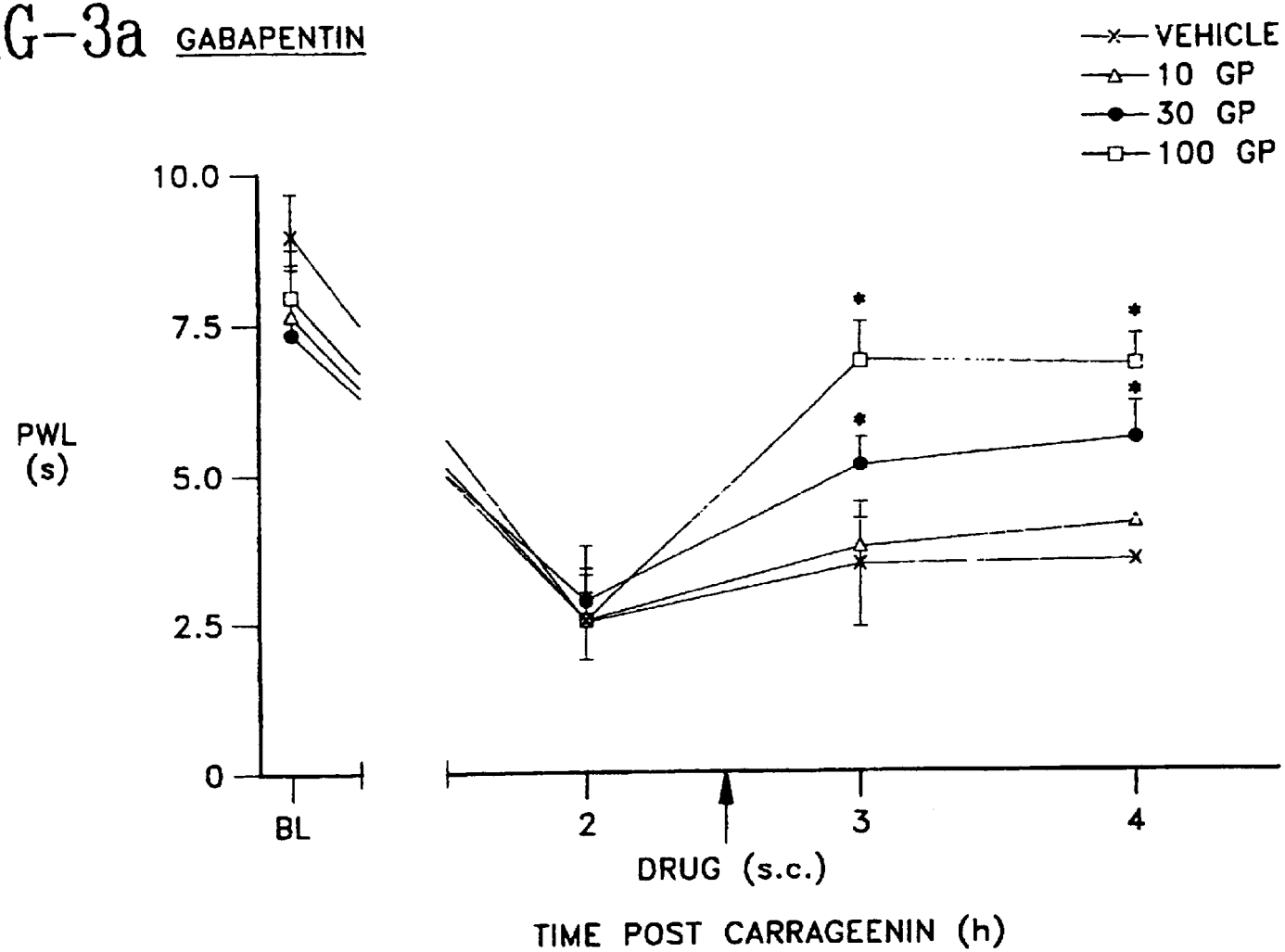

FIG-3b CI-1008
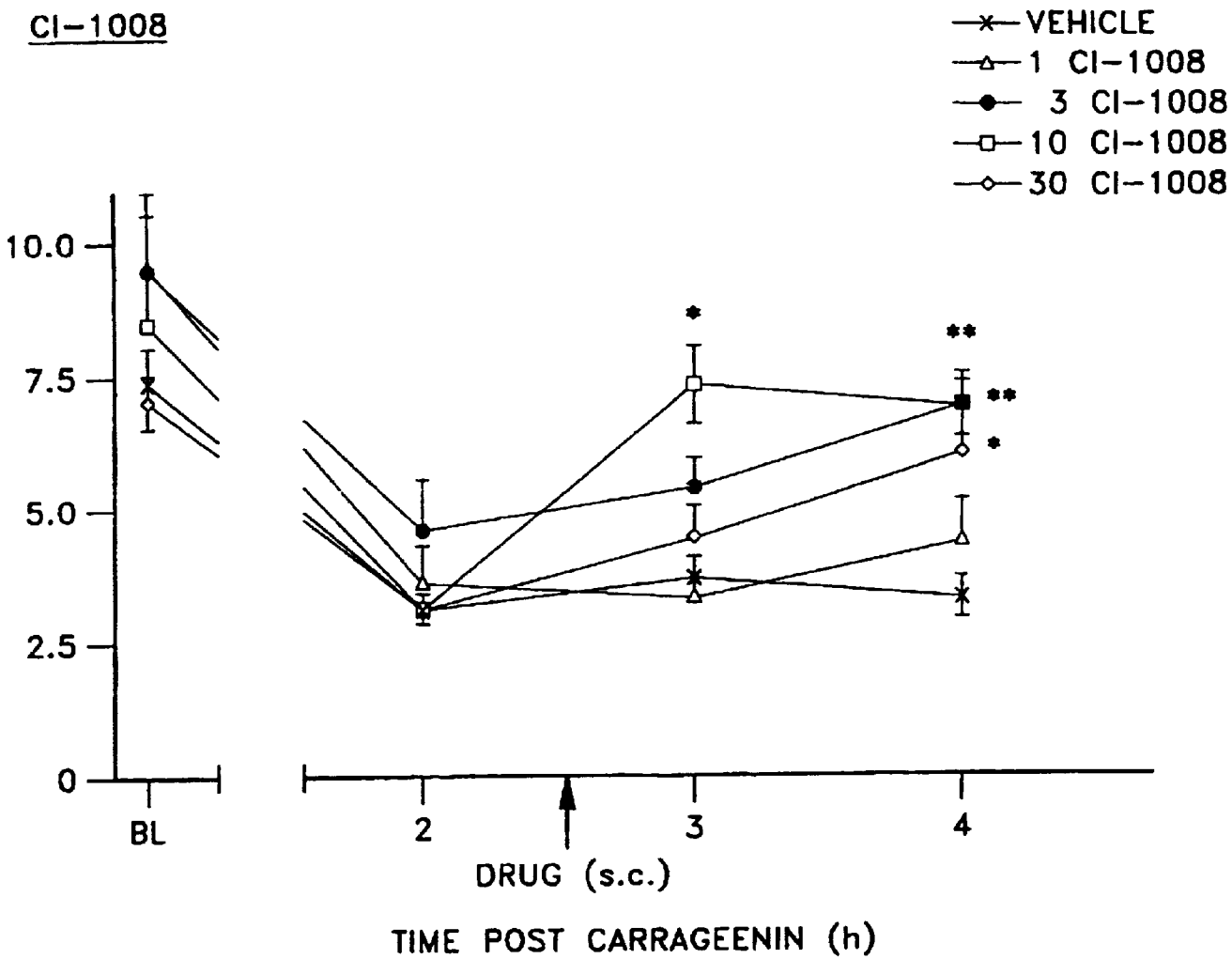

ISOBUTYLGABA AND ITS DERIVATIVES FOR THE TREATMENT OF PAIN

Matter enclosed in heavy brackets [ ] appears in the original patent but forms no part of this reissue specification; matter printed in italics indicates the additions made by reissue.

*Notice: more than one reissue application has been filed for the reissue of U.S. Pat. No. 6,001,876. The reissue applications: are U.S. application Ser. No. 12/700,968 (filed Feb. 5, 2010), which is a continuation of the present application; and, the present application.*

This application claims benefit of Provisional application Ser. No. 60/022,337, Jul. 24, 1996.

BACKGROUND OF THE INVENTION

The present invention is the use of analogs of glutamic acid and gamma-aminobutyric acid (GABA) in pain therapy, as the compounds exhibit analgesic/antihyperalgesic action. Advantages of the use of the compounds includes the finding that repeated use does not lead to tolerance nor is there a cross-tolerance between morphine and the compounds.

The compounds of the invention are known agents useful in antiseizure therapy for central nervous system disorders such as epilepsy, Huntington's chorea, cerebral ischemia, Parkinson's disease, tardive dyskinesia, and spasticity. It has also been suggested that the compounds can be used as antidepressants, anxiolytics, and antipsychotics. See WO 92/09560 (U.S. Ser. No. 618,692 filed Nov. 27, 1990) and WP 93/23383 (U.S. Ser. No. 886,080 filed May 20, 1992).

SUMMARY OF THE INVENTION

The instant invention is a method of using a compound of Formula I below in the treatment of pain, especially for treatment of chronic pain disorders. Such disorders include, but are not limited to, inflammatory pain, postoperative pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, [bum] *burn* pain, and other forms of neuralgic, neuropathic, and idiopathic pain syndromes.

A compound are those of Formula I

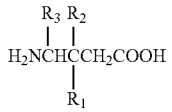

I or a pharmaceutically acceptable salt thereof wherein $R_1$ is a straight or branched alkyl of from 1 to 6 carbon atoms, phenyl, or cycloalkyl of from 3 to 6 carbon atoms;

$R_2$ is hydrogen or methyl; and $R_3$ is hydrogen, methyl, or carboxyl.

Diastereomers and enantiomers of compounds of Formula I are included in the invention.

Preferred compounds of the invention are those according to claim 1 wherein $R_3$ and $R_2$ are hydrogen, and $R_1$ is —$(CH_2)_{0-2}$—i $C_4H_9$ as an (R), (S), or (R,S) isomer.

The more preferred compounds of the invention are (S)-3-(aminomethyl)-5-methylhexanoic acid and 3-aminomethyl-5-methyl-hexanoic acid.

BRIEF DESCRIPTION OF THE DRAWINGS

FIG. 1. Effect of Gabapentin (1-(aminomethyl)-cyclohexaneacetic acid), CI-1008 ((S)-3-(aminomethyl)-5-methylhexanoic acid), and 3-aminomethyl-5-methylhexanoic acid in the Rat Paw Formalin Test Test compounds were administered s.c. 1 hour before an intraplantar injection of 50 μL formalin. The time spent licking/biting the injected paw during the early and late phases was scored. Results are shown as the mean ±SEM of 6 to 8 animals per group. *P<0.05 and **P<0.01 significantly different from vehicle (Veh.) treated controls (ANOVA followed by Dunnett's t-test).

FIG. 2. Effect of Gabapentin and CI-1008 on Carrageenin-Induced Mechanical Hyperalgesia Nociceptive pressure thresholds were measured in the rat using the paw pressure test. Baseline (BL) measurements were taken before animals were administered with 100 μL of 2% carrageenin by intraplantar injection. Results are shown as mean (±SEM) of 8 animals per group. Gabapentin (GP), CI-1008, or morphine (MOR; 3 mg/g) was administered s.c. 3.5 hours after carrageenin. *P<0.05 and **P<0.01 significantly different from vehicle control group at the same time point (ANOVA followed by Dunnett's t-test).

FIG. 3. Effect of Gabapentin and CI-1008 on Carrageenin-Induced Thermal Hyperalgesia Nociceptive thermal thresholds were measured in the rat using the Hargreaves apparatus. Baseline (BL) measurements were taken before animal s were administered with 100 μL of 2% carrageenin by intraplantar injection. Results are shown as mean (±SEM) of 8 animals per group. Gabapentin (GP) or CI-1008 was administered s.c. 2.5 hours after carrageenin. *P<0.05 and **P<0.01 significantly different from vehicle control group at the same time point (ANOVA followed by Dunnett's t-test).

In FIG. 5, —●— is vehicle contralateral, —○— is vehicle ispsilateral. For morphine (5a), —Δ— is 1 mg/kg, —□— is 3, and —◇— is 16.

In 5b for gabapentin and S-(+)-isobutylgaba, —Δ— is 3 mg/kg, —□— is 10, and —◇— is 30.

Figure 4A:
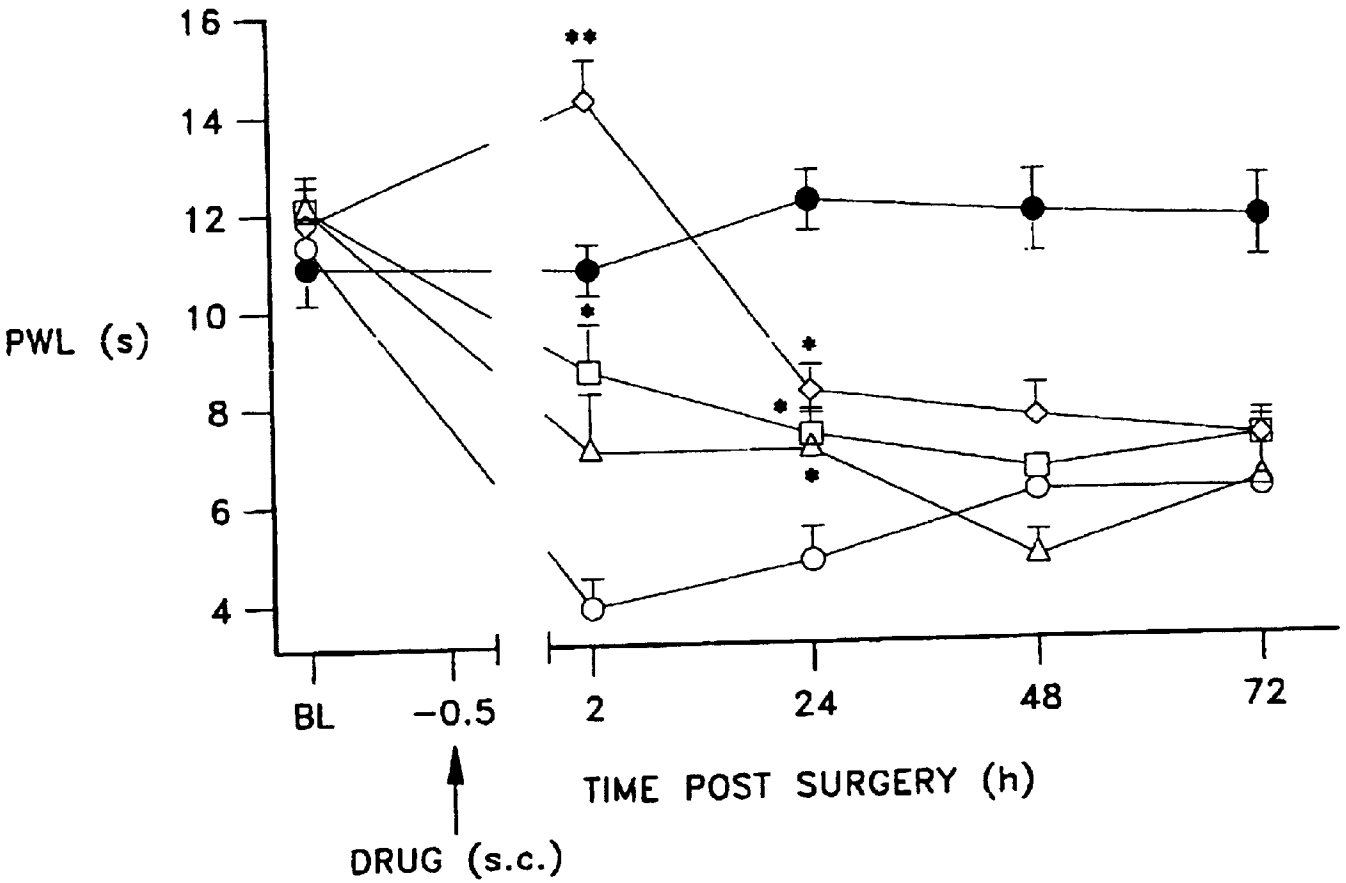
FIG. 4. Effect of (a) Morphine, (b) Gabapentin, and (c) S-(+)-3-Isobutylgaba on Thermal Hyperalgesia in the Rat Postoperative Pain Model Gabapentin or S-(+)-3 isobutylgaba was administered 1 hour before surgery. Morphine was administered 0.5 hour before surgery. Thermal paw withdrawal latencies (PWL) were determined for both ipsilateral and contralateral paws using the rat plantar test. For clarity contralateral paw data for drug-treated animals is not shown. Baseline (BL) measurements were taken before surgery and PWL were reassessed 2, 24, 48, and 72 hours postsurgery. Results are expressed as the mean PWL(s) of 8 to 10 animals per group (vertical bars represent ±SEM). *P<0.05 P<0.01 significantly different (ANOVA followed by Dunnett's t-test), comparing ipsilateral paw of drug-treated groups to ispsilateral paw of vehicle-treated group at each time point. In the figure, —●— is vehicle contralateral, —○— is vehicle ispsilateral, —Δ— is 1 mg/kg morphine, —□— is 3, and —◇— is 6 for morphine in 4a. In 4b, —Δ— is 3, —□— is 10, and —◇— is 30 for gabapentin. In 4**c, —Δ— is 3 mg/kg, —□□— is 10, and —◇— is 30 for S-(+)-isobutylgaba.
Figure 4B:
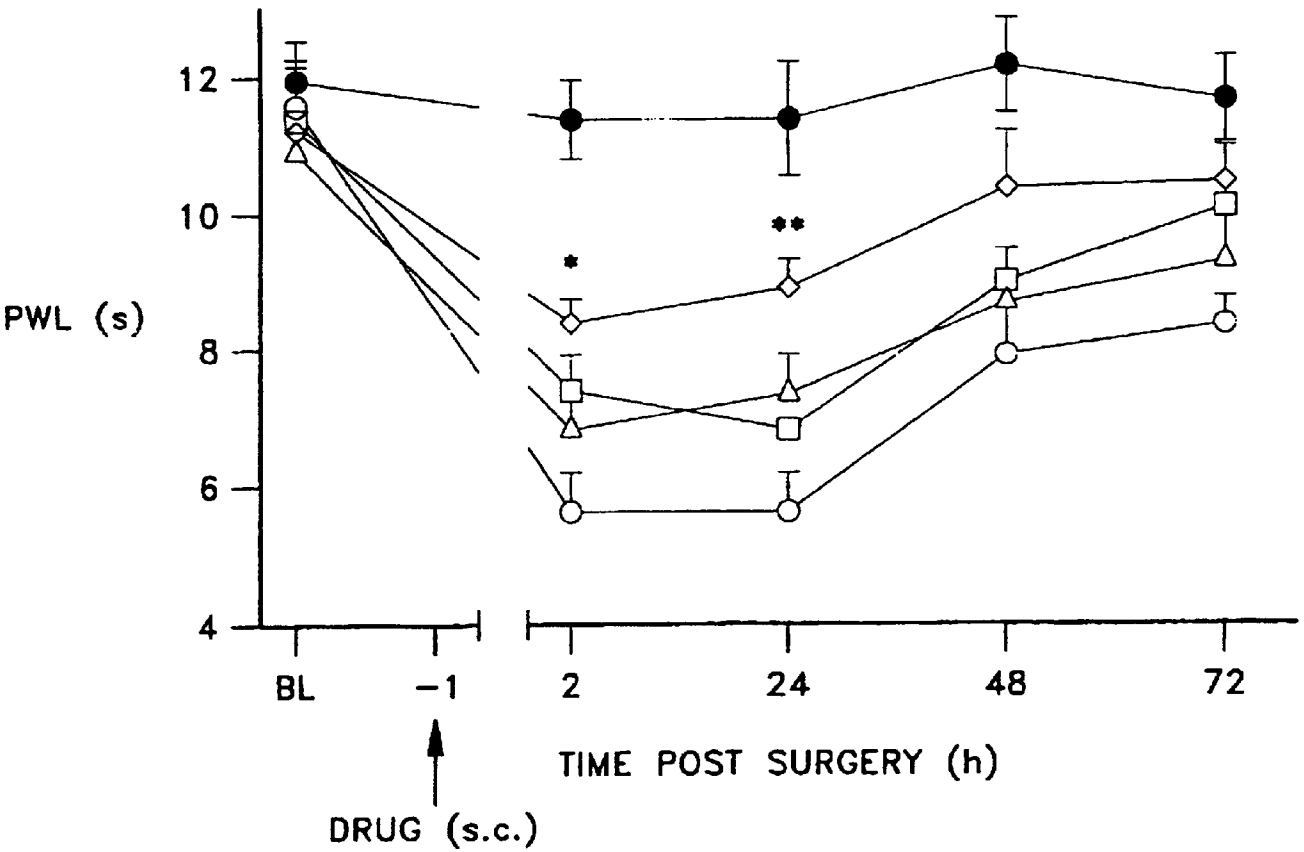
Figure 4C:
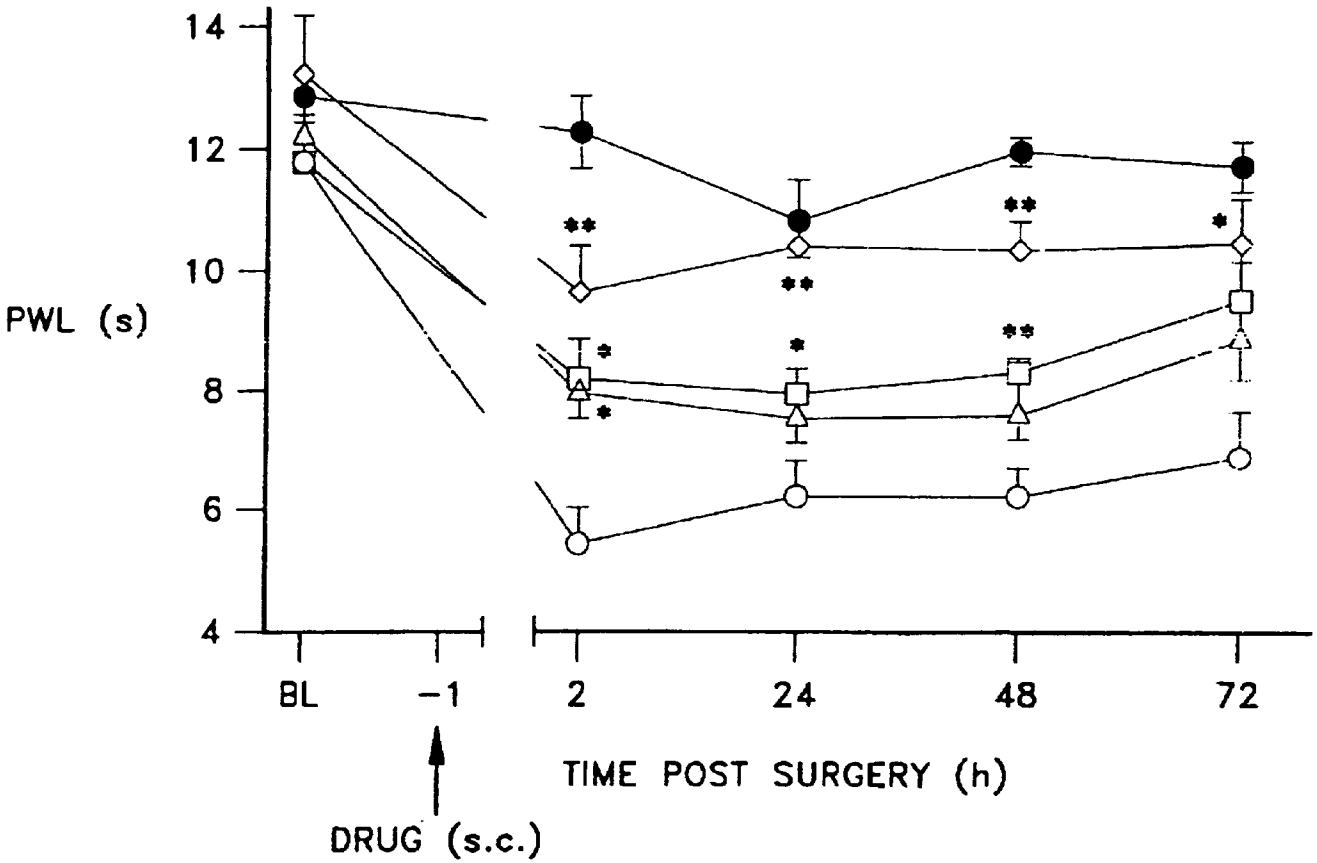
Figure 5A:
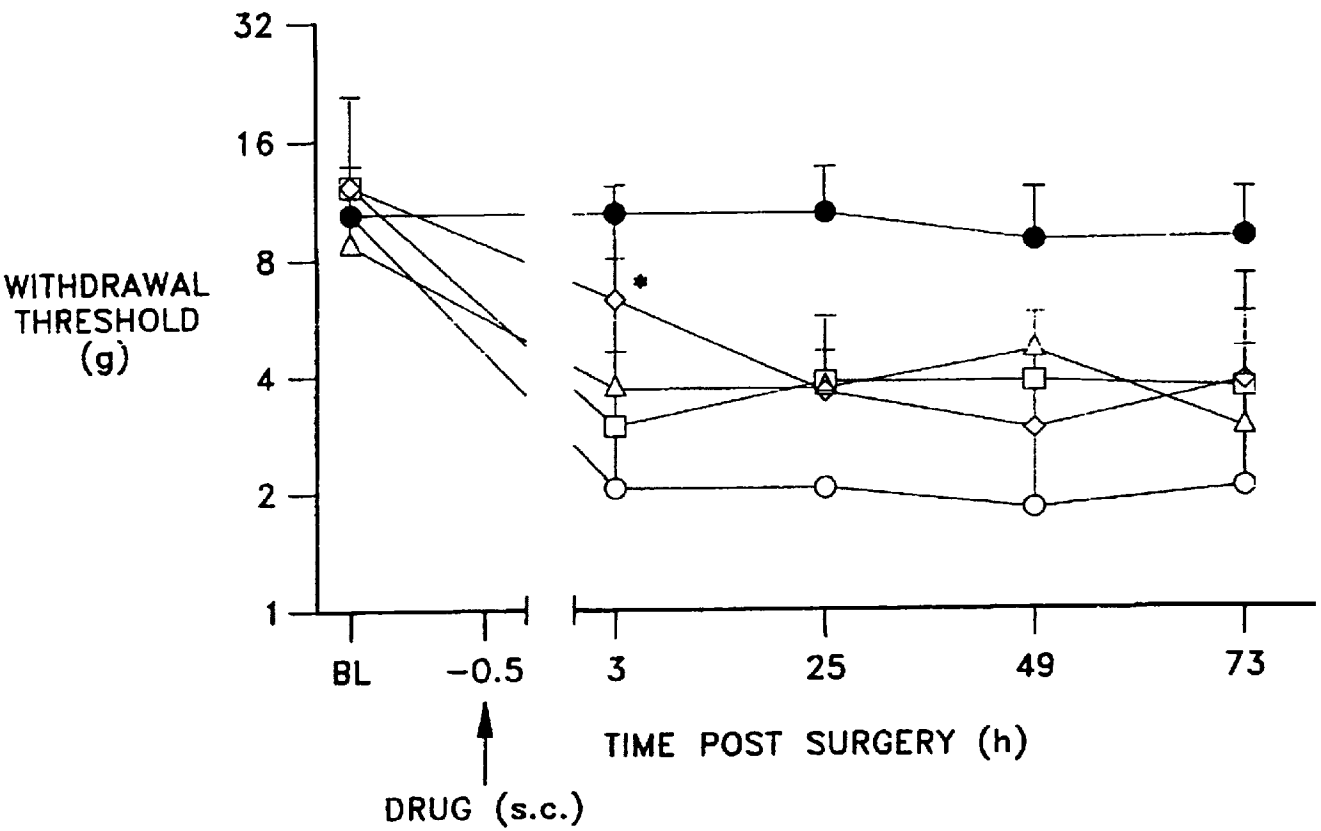
FIG. 5 Effect of (a) Morphine, (b) Gabapentin, and (c) S-(+)-3-Isobutylgaba on Tactile Allodynia in the Rat Postoperative Pain Model Gabapentin or S-(+)-3-isobutylgaba was administered 1 hour before surgery. Morphine was administered 0.5 hour before surgery. Paw withdrawal thresholds to von Frey hair filaments were determined for both ipsilateral and contralateral paws. For clarity, contralateral paw data for drug-treated animals is not shown. Baseline (BL) measurements were taken before surgery, and withdrawal thresholds were reassessed 3, 25, 49, and 73 hours postsurgery. Results are expressed as median force (g) required to induce a withdrawal of paw in 8 to 10 animals per group (vertical bars represent first and third quartiles). *P<0.05 significantly different (Mann Whitney t-test) comparing ipsilateral paw of drug-treated groups to ipsilateral paw of vehicle treated group at each time point.
Figure 5B:
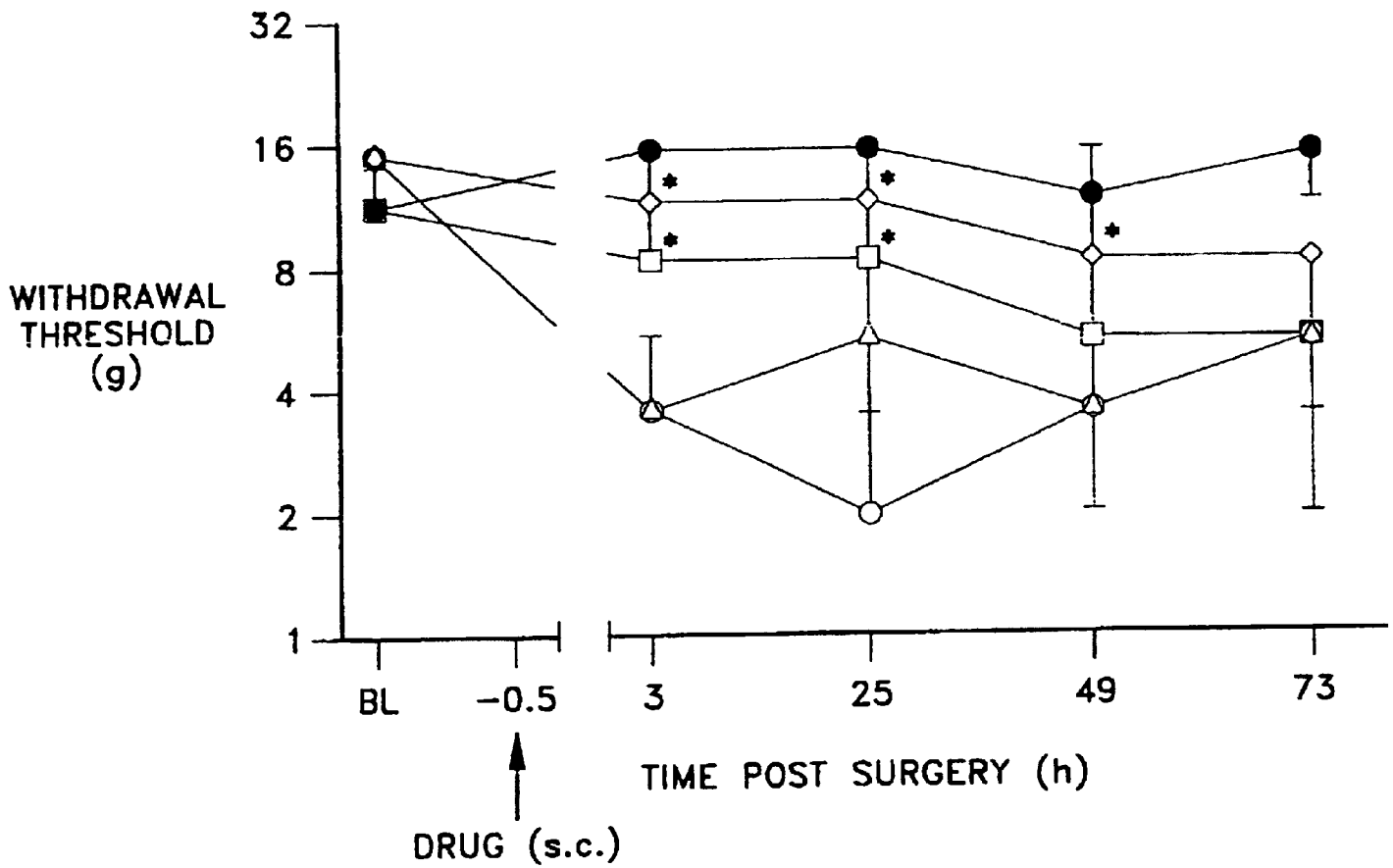
Figure 5C:
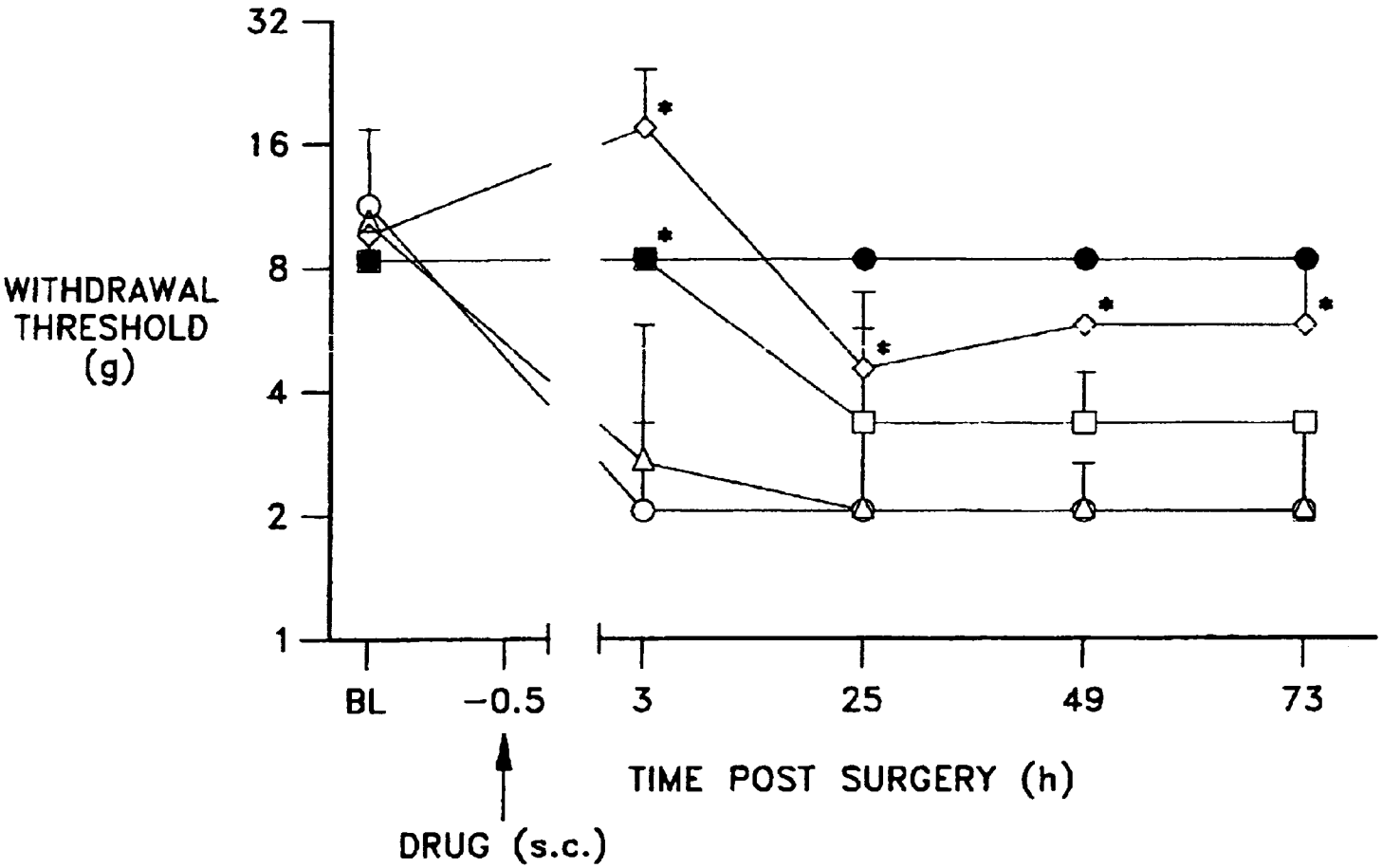
Figure 6A:
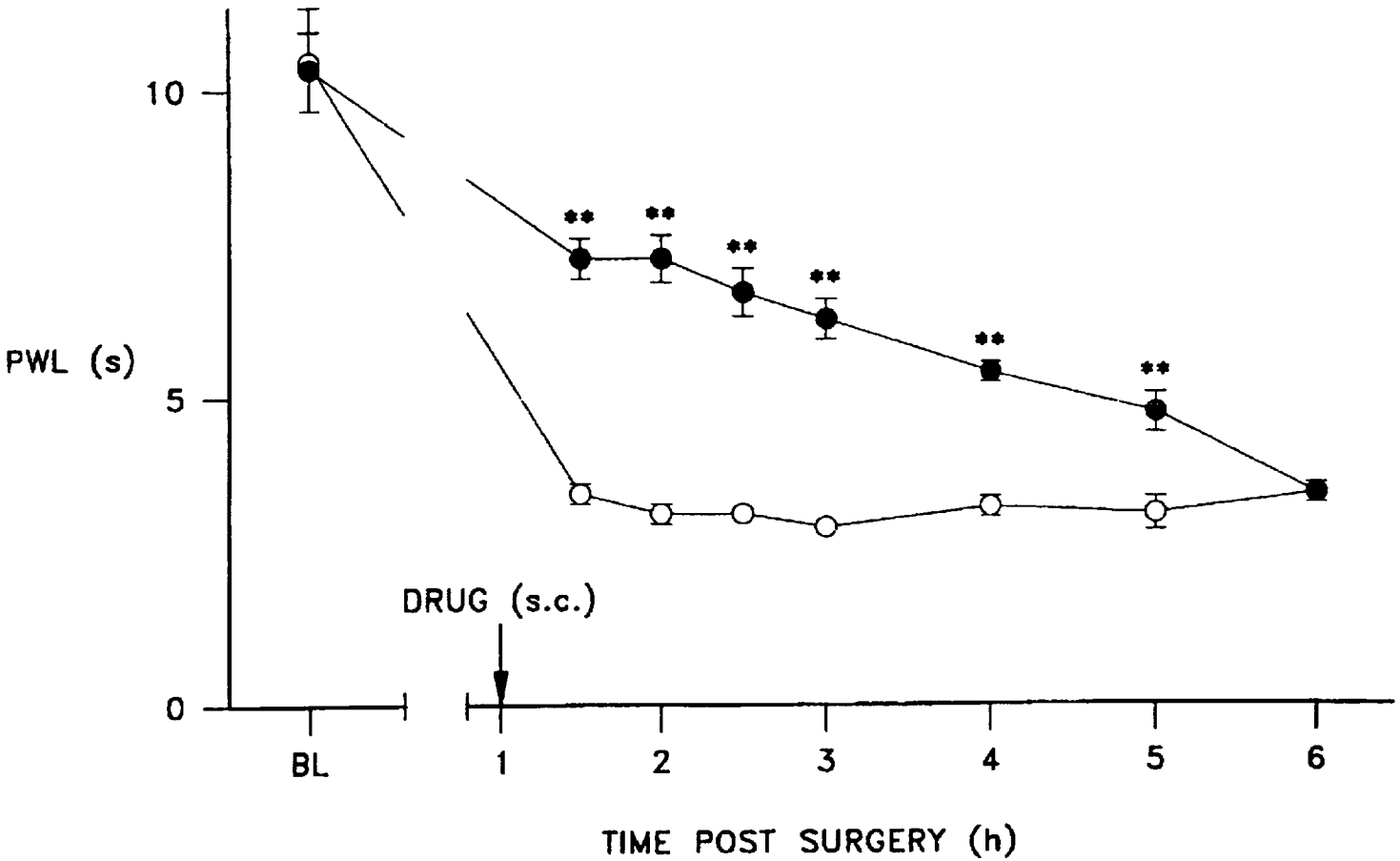
Figure 6B:
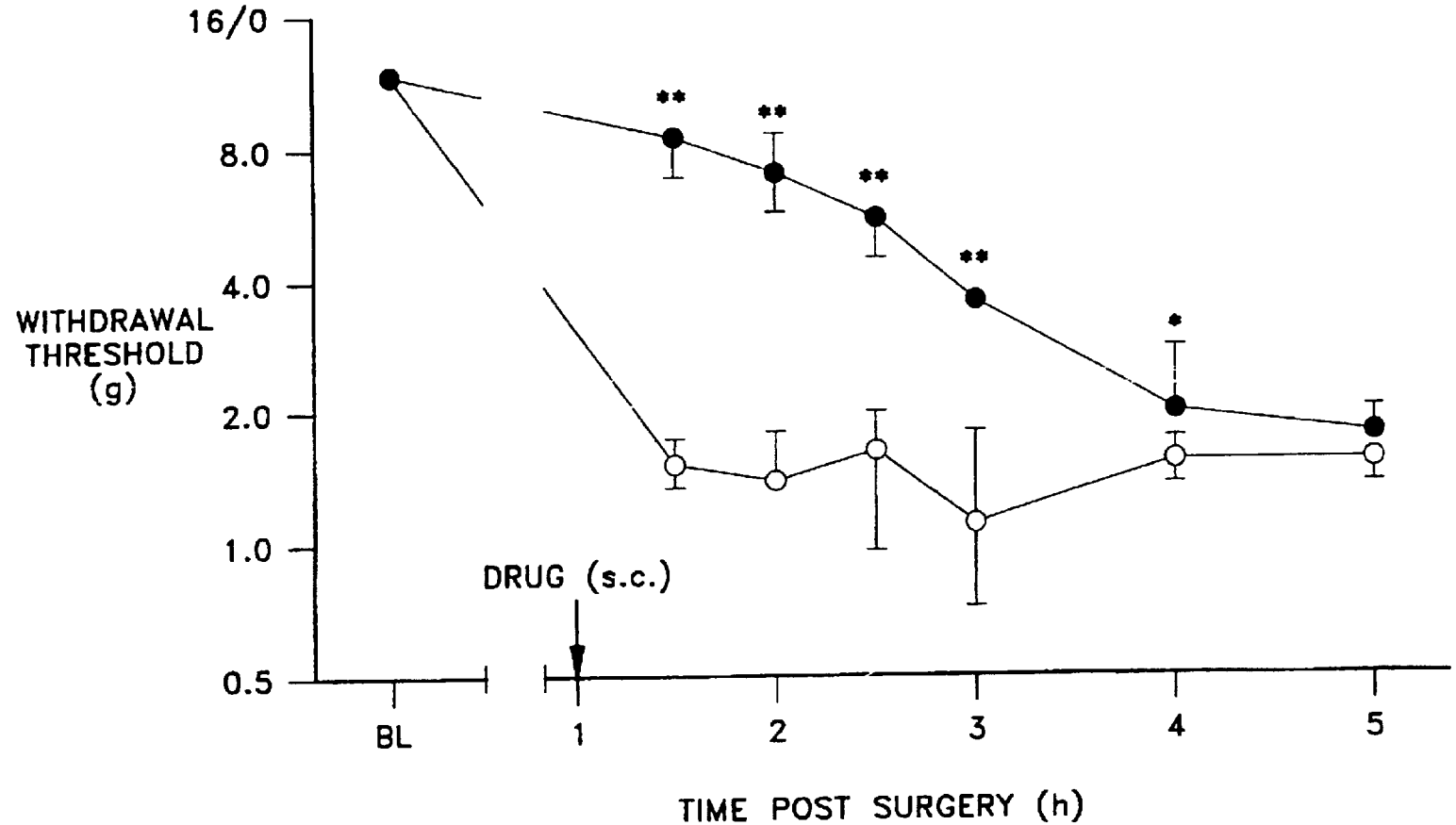

FIG. 6. Effect of S-(+)-3-Isobulylgaba on the Maintenance of (a) Thermal Hyperalgesia and (b) Tactile Allodynia in the Rat Postoperative Pain Model.

S-(+)-3-Isobutylgaba (S-(+)-IBG) was administered 1 hour after surgery. Thermal paw withdrawal latencies, determined using the rat plantar test, and paw withdrawal thresholds to von Frey hair filaments, were determined in separate groups of animals for both ipsilateral and contralateral paws. For clarity only the ipsilateral paw data is shown. Baseline (BL) measurements were taken before surgery and withdrawal thresholds were reassessed up to 6 hours postsurgery. For thermal hyperalgesia, the results are expressed as the mean PWL(s) of 6 animals per group (vertical bars represent ±SEM), *P<0.05 **P<0.01 significantly different (unpaired t-test), comparing ipsilateral paw of drug-treated group to ipsilateral paw of vehicle (Veh —○—) treated group at each time point. For tactile allodynia, the results are expressed as median force (g) required to induce a paw withdrawal of 6 animals per group (vertical bars represent first and third quartiles). *P<0.05 significantly different (Mann Whitney t-test), comparing ipsilateral paw of drug-treated group to ipsilateral paw of vehicle-treated group at each time point. —●— is S-(+)-IBG at 30 mg/kg.

DETAILED DESCRIPTION

The instant invention is a method of using a compound of Formula I above as an analgesic in the treatment of pain as listed above. Pain such as inflammatory pain, neuropathic pain, cancer pain, postoperative pain, and idiopathic pain which is pain of unknown origin, for example, phantom limb pain are included especially. Neuropathic pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

The conditions listed above are known to be poorly treated by currently marketed analgesics such as narcotics or nonsteroidal anti-inflammatory drugs (NSAID) due to insufficient efficacy or limiting side effects.

The terms used in Formula I are, for example, alkyl which term is methyl, ethyl, propyl, isopropyl, n-butyl, isobutyl, sec-butyl, tert-butyl, isopentyl, and neopentyl, as well as those as would occur to one skilled in the art.

The term "cycloalkyl" is exemplified by cyclopropyl, cyclobutyl, cyclopentyl, and cyclohexyl.

The compounds of the present invention may form pharmaceutically acceptable salts with both organic and inorganic acids or bases. For example, the acid addition salts of the basic compounds are prepared either by dissolving the free base in aqueous or aqueous alcohol solution or other suitable solvents containing the appropriate acid and isolating the salt by evaporating the solution. Examples of pharmaceutically acceptable salts are hydrochlorides, hydrobromides, hydrosulfates, etc. as well as sodium, potassium, and magnesium, etc. salts.

The compounds of the present invention can contain one or several asymmetric carbon atoms. The invention includes the individual diastereomers or enantiomers, and the mixtures thereof. The individual diastereomers or enantiomers may be prepared or isolated by methods already well-known in the art.

The method for the formation of the 3-alkyl-4-aminobutanoic acids starting from 2-alkenoic esters is prepared from commercially available aldehydes and monoethyl malonate by the Knoevenagel reaction (Kim Y. C., Cocolase G. H., J. Med. Chem., 1965:8509), with the exception of ethyl 4,4-dimethyl-2-pentenoate. This compound was prepared from 2,2-dimethylpropanal and ethyl lithioacetate, followed by dehydration of the β-hydroxyester with phosphoryl chloride and pyridine. The Michael addition of nitromethane to α,β-unsaturated compounds mediated by 1,1,3,3-tetramethylguanidine or 1,8-diazabicyclo[5.4.0]undec-7-ene(DBU) afforded 4-nitroesters in good yields.

Although the aliphatic nitro compounds are usually reduced by either high pressure catalytic hydrogenation by metal-catalyzed transfer hydrogenation, or by newly introduced hydrogenolysis methods with ammonium formate or sodium borohydride and palladium as catalysts, applicants have found that 4-nitrocarboxylic esters can be reduced almost quantitatively to the corresponding 4-aminocarboxylic esters by hydrogenation using 10% palladium on carbon as catalysts in acetic acid at room temperature and atmospheric pressure. The amino esters produced were subjected to acid hydrolysis to afford the subject inventive compounds in good yields. This procedure provides access to a variety of 3-alkyl-4-aminobutanoic acids as listed in Tables 1 and 2 as examples, and thus is advantageous in comparison to methods previously used.

When the starting material is not commercially available, the synthetic sequence was initiated with the corresponding alcohol, which was oxidized to the aldehyde by the method of Corey, et al., Tetrahedrom. Lett., 1975:2647–2650.

The compounds made by the synthetic methods can be used as pharmaceutical compositions as agent in the treatment of pain when an effective amount of a compound of the Formula I, together with a pharmaceutically acceptable carrier is used. The pharmaceutical can be used in a method for treating such disorders in mammals, including human, suffering therefrom by administering to such mammals an effective amount of the compound as described above in unit dosage form.

The pharmaceutical compound, made in accordance with the present invention, can be prepared and administered in a wide variety of dosage forms by either oral or parenteral routes of administration. For example, these pharmaceutical compositions can be made in inert, pharmaceutically acceptable carriers which are either solid or liquid. Solid form preparations include powders, tablets, dispersible granules, capsules, cachets, and suppositories. Other solid and liquid form preparations could be made in accordance with known methods of the art and administered by the oral route in an appropriate formulation, or by a parenteral route such as intravenous, intramuscular, or subcutaneous injection as a liquid formulation.

The quantity of active compound in a unit dose of preparation may be varied or adjusted from 1 mg to about 300 mg/kg daily, based on an average 70-kg patient. A daily dose range of about 1 mg to about 50 mg/kg is preferred. The dosages, however, may be varied depending upon the requirement with a patient, the severity of the condition being treated, and the compound being employed. Determination of the proper dosage for particular situations is within the skill of the art.

Effects of Gabapentin, CI-1008, and 3-Aminomethyl-5-methyl-hexanoic Acid in the Rat Formalin Paw Test Male Sprague-Dawley rats (70–90 g) were habituated to perspex observation chambers (24 cm×24 cm×24 cm) for at least 15 minutes prior to testing. Formalin-induced hind paw licking and biting was initiated by a 50 μL subcutaneous injection of a 5% formalin solution (5% formaldehyde in isotonic saline) into the plantar surface of the left hind paw. Immediately following the formalin injection, licking/biting of the injected hind paw was scored in 5 minute bins for 60 minutes. The results are expressed as mean combined licking/biting time for the early phase (0–10 minutes) and late phase (10–45 minutes).

The s.c. administration of gabapentin (10–300 mg/kg) or CI-1008 (1–100 mg/kg) 1 hour before formalin dose-dependently blocked the licking/biting behavior during the late phase of the formalin response with respective minimum effective doses (MED) of 30 and 10 mg/kg (FIG. 1). However, neither of the compounds affected the early phase at any of the doses tested. Similar administration of 3-aminomethyl-5-methyl-hexanoic acid produced only a modest blockade of the late phase at 100 mg/kg.

Effects of Gabapentin and CI-1008 on Carrageenin-Induced Hyperalgesia

On the test Day, 2 to 3 baseline measurements were taken before rats (male Sprague-Dawley 70–90 g) were administered with 100 μL of 2% carrageenin by intraplantar injection into the right hind paw. Animals were dosed with the test drug after development of peak hyperalgesia. Separate groups of animals were used for the mechanical and thermal hyperalgesia studies.

A. Mechanical Hyperalgesia

Nociceptive pressure thresholds were measured in the rat paw pressure test using an analgesimeter (Ugo Basile). A cut-off point of 250 g was used to prevent any damage to the paw. The intraplantar injection of carrageenin produced a reduction in the nociceptive pressure threshold between 3 and 5 hours after injection, indicating induction of hyperalgesia. Morphine (3 mg/kg, s.c.) produced a complete blockade of hyperalgesia (FIG. 2). Gabapentin (3–300 mg/kg, s.c.) and CI-1008 (1–100 mg/kg, s.c.) dose-dependently antagonized the hyperalgesia, with respective MED of 10 and 3 mg/kg (FIG. 2).

B. Thermal Hyperalgesia

Baseline paw withdrawal latencies (PWL) were obtained for each rat using the Hargreaves model. Carrageenin was injected as described above. Animals were then tested for thermal hyperalgesia at 2 hours postcarrageenin administration. Gabapentin (10–100 mg/kg) or CI-1008 (1–30 mg/kg) was administered s.c. 2.5 hours after carrageenin, and PWL were reevaluated at 3 and 4 hours postcarrageenin administration. Carrageenin induced a significant reduction in paw withdrawal latency at 2, 3, and 4 hours following injection, indicating the induction of thermal hyperalgesia (FIG. 3). Gabapentin and CI-1008 dose-dependently antagonized the hyperalgesia with a MED of 30 and 3 mg/kg (FIG. 3).

These data show that gabapentin and CI-1008 are effective in the treatment of inflammatory pain.

The assay of Bennett G. J. provides an animal model of a peripheral mononeuropathy in rat that produces disorder of pain sensation like those seen in man (Pain, 1988;33:87–107).

The assay of Kim S. H., et al., provides one experimental model for peripheral neuropathy produced by segmented spinal nerve ligation in the rat (Pain, 1990;50:355–363).

A rat model of postoperative pain has been described (Brennan et al., 1996). It involves an incision of the skin, fascia, and muscle of the plantar aspect of the hind paw. This leads to an induction of reproducible and quantifiable mechanical hyperalgesia lasting several days. It has been suggested that this model displays some similarities to the human postoperative pain state. In the present study we have examined and compared the activities of gabapentin and S-(+)-3-isobutylgaba with morphine in this model of post-operative pain.

METHODS

Male Sprague-Dawley rats (250–300 g), obtained from Bantin and Kingmen, (Hull, U. K.) were used in all experiments. Before surgery, animals were housed in groups of 6 under a 12-hour light/dark cycle (lights on at 07 hour 00 minute) with food and water ad libitum. Postoperatively, animals were housed in pairs on "Aqua-sorb" bedding consisting of air laid cellulose (Beta Medical and Scientific, Sale, U.K.) under the same conditions. All experiments were carried out by an observer blind to drug treatments.

Surgery

Animals were anaesthetized with 2% isofluorane and 1.4 $O_2/NO_2$ mixture which was maintained during surgery via a nose cone. The plantar surface of the right hind paw was prepared with 50% ethanol, and a 1-cm longitudinal incision was made through skin and fascia, starting 0.5 cm from the edge of the heel and extending towards the toes. The plantaris muscle was elevated using forceps and incised longitudinally. The wound was closed using two simple sutures of braided silk with a FST-02 needle. The wound site was covered with Terramycin spray and Auromycin powder. Postoperatively, none of the animals displayed any signs of infection with the wounds healing well after 24 hours. The sutures were removed after 48 hours.

Evaluation of Thermal Hyperalgesia

Thermal hyperalgesia was assessed using the rat plantar test (Ugo Basile, Italy) following a modified method of Hargreaves, et al., 1988. Rats were habituated to the apparatus which consisted of three individual perspex boxes on an elevated glass table. A mobile radiant heat source was located under the table and focused onto the hind paw and paw withdrawal latencies (PWL) were recorded. There was an automatic cut off point of 22.5 seconds to prevent tissue damage. PWLs were taken 2 to 3 times for both hind paws of each animal, the mean of which represented baselines for right and left hind paws. The apparatus was calibrated to give a PWL of approximately 10 seconds. PWL(s) were reassessed following the same protocol as above 2, 24, 48, and 72 hours postoperatively.

Evaluation of Tactile Allodynia

Tactile allodynia was measured using Semmes-Weinstein von Frey hairs (Stoelting, Ill., U.S.A.). Animals were placed into wire-mesh-bottom cages allowing access to the underside of their paws. The animals were habituated to this environment prior to the start of the experiment. Tactile allodynia was tested by touching the plantar surface of the animals hind paw with von Frey hairs in ascending order of force (0.7, 1.2, 1.5, 2, 3.6, 5.5, 8.5, 11.8, 15. 1, and 29 g) until a paw withdrawal response was elicited. Each von Frey hair was applied to the paw for 6 seconds, or until a response occurred. Once a withdrawal response was established, the paw was retested, starting with the next descending von Frey hair until no response occurred. The highest force of 29 g lifted the paw as well as eliciting a response, thus represented the cut-off point. Each animal had both hind paws tested in this manner. The lowest amount of force required to elicit a response was recorded as withdrawal threshold in grams. When compounds were administered before surgery, the same animals were used to study drug effects on tactile, allodynia, and thermal hyperalgasia, with each animal being tested for tactile allodynia 1 hour after thermal hyperalgesia. Separate groups of animals were used for examination of tactile allodynia and thermal hyperalgesia when S-(+)-3-isobutylgaba was administered after surgery.

Statistics

Data obtained for thermal hyperalgesia was subjected to a one-way (analysis of variance) ANOVA followed by a Dunnett's t-test. Tactile allodynia results obtained with the von Frey hairs were subjected to an individual Mann Whitney t-test.

RESULTS

An incision of the rat plantaris muscle led to an induction of thermal hyperalgesia and tactile allodynia. Both nociceptive responses peaked within 1 hour following surgery and were maintained for 3 days. During the experimental period, all animals remained in good health.

Effect of Gabapentin. S-(+)-3-Isobutylgaba and Morphine Administered Before Surgery on Thermal Hyperalgesia The single-dose administration of gabapentin 1 hour before surgery dose-dependently (3–30 mg/kg, s.c.) blocked development of thermal hyperalgesia with a MED of 30 mg/kg (FIG. 1b). The highest dose of 30 mg/kg gabapentin prevented the hyperalgesic response for 24 hours (FIG. 1b). Similar administration of S-(+)-3-isobutylgaba also dose-dependently (3–30 mg/kg, s.c.) prevented development of thermal hyperalgesia with a MED of 3 mg/kg (FIG. 1c). The 30 mg/kg dose of S-(+)-3-isobutylgaba was effective up to 3 days (FIG. 1c). The administration of morphine 0.5 hour before surgery dose-dependently (1–6 mg/kg, s.c.) antagonized the development of thermal hyperalgesia with a MED of 1 mg/kg (FIG. 1a). This effect was maintained for 24 hours (FIG. 1a).

Effects of Gabapentin, S-(+)-3-Isobutylgaba and Morphine Administered Before Surgery on Tactile Allodynia The effect of drugs on development of tactile allodynia was determined in the same animals used for thermal hyperalgesia above. One hour was allowed between thermal hyperalgesia and tactile allodynia tests. Gabapentin dose-dependently prevented development of tactile allodynia with a MED of 10 mg/kg. The 10 and 30 mg/kg doses of gabapentin were effective for 25 and 49 hours, respectively (FIG. 2b). S-(+)-3-Isobutylgaba also dose-dependently (3–30 mg/kg) blocked development of the allodynia response with a MED of 10 mg/kg (FIG. 2c). This blockade of the nociceptive response was maintained for 3 days by the 30 mg/kg dose of S-(+)-3-isobutylgaba (FIG. 2c). In contrast, morphine (1–6 mg/kg) only prevented the development of tactile allodynia for 3 hour postsurgery at the highest dose of 6 mg/kg (FIG. 2a).

Effect of S-(+)-3-Isobutylgaba Administered 1 Hour After Surgery on Tactile Allodynia and Thermal Hyperalgesia The allodynia and hyperalgesia peaked within 1 hour in all animals and was maintained for the following 5 to 6 hours. The s.c. administration of 30 mg/kg S-(+)-3-isobutylgaba 1 hour after surgery blocked the maintenance of tactile allodynia and thermal hyperalgesia for 3 to 4 hours. After this time, both nociceptive responses returned to control levels indicating disappearance of antihyperalgesic and antiallodynic actions (FIG. 3).

Gabapentin and S-(+)-3-isobutylgaba did not affect PWL in the thermal hyperalgesia test or tactile allodynia scores in the contralateral paw up to the highest dose tested in any of the experiments. In contrast, morphine (6 mg, s.c.) increased PWL of the contralateral paw in the thermal hyperalgesia test (data not shown).

The results presented here show that incision of the rat plantaris muscle induces thermal hyperalgesia and tactile allodynia lasting at least 3 days. The major findings of the present study are that gabapentin and S-(+)-3-isobutylgaba are equally effective at blocking both nociceptive responses. In contrast, morphine was found to be more effective against thermal hyperalgesia than tactile allodynia. Furthermore, S-(+)-3-isobutylgaba completely blocked induction and maintenance of allodynia and hyperalgesia.

What is claimed is:

[1. A method for treating pain comprising administering a therapeutically effective amount of a compound of Formula I

I

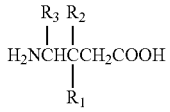

or a pharmaceutically acceptable salt, diastereomer, or enantiomer thereof wherein $R_1$ is a straight or branched alkyl of from 1 to 6 carbon atoms, phenyl, or cycloalkyl of from 3 to 6 carbon atoms;

$R_2$ is hydrogen or methyl; and $R_3$ is hydrogen, methyl, or carboxyl to a mammal in need of said treatment.]

2. A method [according to claim 1] *for treating pain comprising administering a therapeutically effective amount of a compound of Formula I*

*I*

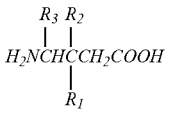

*or a pharmaceutically acceptable salt thereof,* [wherein the compound administered is a compound of Formula I] wherein $R_3$ and $R_2$ are hydrogen, and $R_1$ is [—$(CH_2)_{0-2}$—i $C_4H_9$] *isobutyl* as an [(R),] (S)[, or (R,S)] isomer*, to a mammal in need of said treatment.*

[3. A method according to claim 1 wherein the compound administered is named (S)-3-(aminomethyl)-5-methylhexanoic acid and 3-aminomethyl-5-methylhexanoic acid.]

4. A method according to claim [1] *2* wherein the pain treated is inflammatory pain.

5. A method according to claim [1] *2* wherein the pain treated is neuropathic pain.

6. A method according to claim [1] *2* wherein the pain treated is cancer pain.

7. A method according to claim [1] *2* wherein the pain treated is postoperative pain.

8. A method according to claim [1] *2* wherein the pain treated is phantom [limit] *limb* pain.

9. A method according to claim [1] *2* wherein the pain treated is [bum] *burn* pain.

10. A method according to claim [1] *2* wherein the pain treated is gout pain.

11. A method according to claim [1] *2* wherein the pain treated is osteoarthritic pain.

12. A method according to claim [1] *2* wherein the pain treated is trigeminal neuralgia pain.

13. A method according to claim [1] *2* wherein the pain treated is acute herpetic and postherpetic pain.

14. A method according to claim [1] *2* wherein the pain treated is causalgia pain.

15. A method according to claim [1] *2* wherein the pain treated is idiopathic pain.

*16. A method for treating pain comprising administering a therapeutically effective amount of (S)-3-(aminomethyl)-5-methylhexanoic acid, or a pharmaceutically acceptable salt thereof, to a human in need of said treatment.*

*17. A method according to claim 16 wherein the compound administered is (S)-3-(aminomethyl)-5-methylhexanoic acid.*

*18. A method according to claim 16 wherein the compound administered is a pharmaceutically acceptable salt of (S)-3-(aminomethyl)-5-methylhexanoic acid.*

*19. A method according to claim 17 wherein the pain treated is chronic pain.*

*20. A method according to claim 17 wherein the pain treated is selected from the group consisting of inflammatory pain, neuropathic pain, cancer pain, postoperative pain, and idiopathic pain.*

*21. A method according to claim 17 wherein the pain treated is neuropathic pain.*

*22. A method according to claim 17 wherein the pain treated is diabetic neuropathic pain.*

*23. A method according to claim 17 wherein the pain treated is acute herpetic pain.*

*24. A method according to claim 17 wherein the pain treated is postherpetic pain.*

*25. A method according to claim 17 wherein the pain treated is fibromyalgia pain.*

* * * * *